(12) United States Patent
Lee et al.

(10) Patent No.: US 10,786,591 B2
(45) Date of Patent: Sep. 29, 2020

(54) CONTAMINANT REDUCING DEVICE

(71) Applicant: SAMSUNG HEAVY INDUSTRIES CO., LTD., Seoul (KR)

(72) Inventors: Seung Jae Lee, Gyeongsangnam-do (KR); Hee Jun Park, Gyeongsangnam-do (KR); Gun Il Park, Gyeongsangnam-do (KR)

(73) Assignee: SAMSUNG HEAVY INDUSTRIES CO., LTD., Seoul (KR)

( * ) Notice: Subject to any disclaimer, the term of this patent is extended or adjusted under 35 U.S.C. 154(b) by 218 days.

(21) Appl. No.: 15/758,333

(22) PCT Filed: Mar. 28, 2016

(86) PCT No.: PCT/KR2016/003156
§ 371 (c)(1),
(2) Date: Mar. 7, 2018

(87) PCT Pub. No.: WO2017/043722
PCT Pub. Date: Mar. 16, 2017

(65) Prior Publication Data
US 2018/0243461 A1 Aug. 30, 2018

(30) Foreign Application Priority Data

Sep. 10, 2015 (KR) .................. 10-2015-0128596
Sep. 16, 2015 (KR) .................. 10-2015-0131169
Jan. 6, 2016 (KR) .................. 10-2016-0001669

(51) Int. Cl.
*A61L 9/20* (2006.01)
*B01D 47/06* (2006.01)
(Continued)

(52) U.S. Cl.
CPC ................ *A61L 9/20* (2013.01); *B01D 47/06* (2013.01); *B01D 53/78* (2013.01); *F01N 3/037* (2013.01);
(Continued)

(58) Field of Classification Search
CPC .......... A61L 9/20; B01D 47/06; B01D 53/78; B01D 2257/302; B01D 2257/404;
(Continued)

(56) References Cited

U.S. PATENT DOCUMENTS

2014/0140913 A1  5/2014  Suchak
2014/0161678 A1  6/2014  Shin et al.
2014/0248201 A1*  9/2014  Hansen .................. B01D 47/00
                                                            423/212

FOREIGN PATENT DOCUMENTS

CN   103842051 A   6/2014
CN   104470622 A   3/2015
(Continued)

OTHER PUBLICATIONS

Machine Translation JP 2003-284919 (Year: 2019).*
(Continued)

*Primary Examiner* — Thai Ba Trieu
*Assistant Examiner* — Dapinder Singh
(74) *Attorney, Agent, or Firm* — SoCal IP Law Group LLP; Mark Andrew Goldstein

(57) ABSTRACT

A contaminant reducing device is provided. The contaminant reducing device comprises: an exhaust gas tube for supplying exhaust gas from a combustion engine; a cleaning water supply tube for supplying cleaning water; a scrubber for spraying cleaning water, which is supplied through the cleaning water supply tube, to exhaust gas supplied through the exhaust gas tube; an oxidation unit connected to the exhaust gas tube so as to oxidize the exhaust gas by
(Continued)

discharging electricity, emitting ultraviolent rays, or spraying an oxidizer; and a cleaning water discharge tube for discharging cleaning water from inside the scrubber.

15 Claims, 16 Drawing Sheets

(51) Int. Cl.
  *B01D 53/78*    (2006.01)
  *F01N 3/08*    (2006.01)
  *F01N 3/04*    (2006.01)
  *H01M 8/0656*    (2016.01)
  *F01N 3/28*    (2006.01)
  *F01N 3/037*    (2006.01)
  *H01M 8/1018*    (2016.01)

(52) U.S. Cl.
  CPC .............. *F01N 3/04* (2013.01); *F01N 3/0821* (2013.01); *F01N 3/0892* (2013.01); *F01N 3/2896* (2013.01); *H01M 8/0656* (2013.01); *B01D 2221/08* (2013.01); *B01D 2247/04* (2013.01); *B01D 2251/10* (2013.01); *B01D 2251/108* (2013.01); *B01D 2252/1035* (2013.01); *B01D 2257/302* (2013.01); *B01D 2257/404* (2013.01); *B01D 2259/4566* (2013.01); *F01N 2240/05* (2013.01); *F01N 2240/28* (2013.01); *F01N 2240/32* (2013.01); *F01N 2590/02* (2013.01); *F01N 2610/01* (2013.01); *H01M 2008/1095* (2013.01); *Y02A 50/20* (2018.01)

(58) Field of Classification Search
  CPC ........ B01D 2252/1035; B01D 2251/10; B01D 2251/108; B01D 2259/4566; B01D 2247/04; B01D 2221/08; F01N 3/0892; F01N 3/0821; F01N 3/04; F01N 3/037; F01N 3/2896; F01N 2590/02; F01N 2240/32; F01N 2240/05; F01N 2240/28; F01N 2610/01; H01M 8/0656; H01M 2008/1095; Y02A 50/2328
  USPC .... 60/286, 295, 297, 299–301, 311; 95/224; 429/412
  See application file for complete search history.

(56) References Cited

FOREIGN PATENT DOCUMENTS

| | | | |
|---|---|---|---|
| EP | 1859158 | A1 | 11/2007 |
| FR | 3013381 | A1 | 5/2015 |
| JP | 3617405 | A | 9/2001 |
| JP | 2003104292 | A | 4/2003 |
| JP | 2003-284919 | A | 10/2003 |
| JP | 2004089770 | A | 3/2004 |
| JP | 2005125319 | A | 5/2005 |
| JP | 2010513710 | A | 4/2010 |
| JP | 2013050080 | A | 3/2013 |
| JP | 2014012996 | A | 1/2014 |
| JP | 2014055567 | A | 3/2014 |
| JP | 2014104430 | A | 6/2014 |
| KR | 0167793 | B1 | 1/1999 |
| KR | 200187104 | Y1 | 6/2000 |
| KR | 10-2007-0010623 | | 1/2007 |
| KR | 10-20070043352 | | 4/2007 |
| KR | 10-2012-0019660 | | 3/2012 |
| KR | 2012-0019660 | A | 3/2012 |
| KR | 10-2012-0114182 | A | 10/2012 |
| KR | 2013-0048563 | A | 5/2013 |
| KR | 10-2013-0115503 | | 10/2013 |
| KR | 10-2014-0065119 | | 5/2014 |
| KR | 10-2014-0123665 | A | 10/2014 |
| KR | 10-2015-0024437 | | 3/2015 |
| KR | 101514195 | B1 | 4/2015 |
| KR | 101551806 | B1 | 9/2015 |
| WO | 2017043722 | A1 | 3/2017 |

OTHER PUBLICATIONS

Machine translation KR 10-1551806 (Year: 2019).*
World Intellectual Property Organization, International Search Report for international application No. PCT/KR2016/003156, dated Jul. 5, 2016, 5 total pages.
Korean Intellectual Property Office, Office Action for Korean No. 10-2015-0128596, dated Nov. 29, 2016, 3 total pages.
Korean Intellectual Property Office, Office Action for Korean No. 10-2015-0131169, dated Dec. 2, 2016, 4 total pages.
Korean Intellectual Property Office, Notice of Allowance for Korean No. 10-2016-0001669, dated Jul. 10, 2017, 1 page.
Korean Intellectual Property Office, Office Action for Korean No. 10-2016-0001669, dated Mar. 24, 2017, 5 total pages.
European Union Intellectual Property Office, Partial European Search Report for application No. EP 16844542.7, dated Feb. 5, 2019, 13 total pages.
Chinese Intellectual Property Office, Office Action for application No. 201680052334.0, dated Jul. 30, 2019, 9 total pages.
Japanese Intellectual Property Office, Office Action for Japanese application No. JP 2018-508218, dated Dec. 10, 2018, 4 total pages.
Chinese Intellectual Property Office, Second Office Action for application No. 201680052334.0, dated Apr. 10, 2020, 10 total pages.

* cited by examiner

CONTAMINANT REDUCING DEVICE

RELATED APPLICATION INFORMATION

This patent claims priority from International PCT Patent Application No. PCT/KR2016/003156, filed Mar. 28, 2016 entitled, "CONTAMINANT REDUCING DEVICE", which claims priority to Korean Patent Application Nos. 10-2015-0128596, filed Sep. 10, 2015, 10-2015-0131169, filed Sep. 16, 2015 and 10-2016-0001669, filed Jan. 6, 2016, all of which are incorporated herein by reference in their entirety.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

The present inventive concept relates to a contaminant reducing device, and more particularly, to a contaminant reducing device which can remove contaminants from exhaust gas supplied from a combustion engine and then discharge the exhaust gas.

Generally, various engines installed in a ship generate power by burning fossil fuels. Here, exhaust gas generated in the fuel combustion process contains harmful substances such as sulfur oxides (SOx), nitrogen oxides (NOx), and fine dust (PM). Thus, if the exhaust gas is discharged as it is, it can cause air pollution.

For this reason, environmental regulations on air pollution caused by ships are being strengthened, and various treatment devices are being applied to ships in order to meet various regulations. Of the environmental regulations on air pollution, the regulation that requires the sulfur oxide content of exhaust gas emitted from an engine to be 0.1% or less while a ship is travelling or docking in an emission control area (ECA) is in effect. To remove sulfur oxides, ultralow sulfur fuel having a sulfur content of 0.1% or less may be used, or a wet scrubber may be applied. The wet scrubber removes sulfur oxides by bringing exhaust gas into contact with seawater, fresh water or an alkaline solution.

CITATION LIST

Korean Patent Publication No. 10-2014-0123665 (published on Oct. 23, 2014)

DISCLOSURE

Technical Problem

Aspects of the inventive concept provide a contaminant reducing device which can remove contaminants from exhaust gas supplied from a combustion engine and then discharge the exhaust gas.

However, aspects of the inventive concept are not restricted to the one set forth herein. The above and other aspects of the inventive concept will become more apparent to one of ordinary skill in the art to which the inventive concept pertains by referencing the detailed description of the inventive concept given below.

Technical Solution

According to an aspect of the inventive concept, there is provided a contaminant reducing device including: an exhaust gas tube which supplies exhaust gas from a combustion engine; a cleaning water supply tube which supplies cleaning water; a scrubber which sprays the cleaning water supplied through the cleaning water supply tube to the exhaust gas supplied through the exhaust gas tube; an oxidation unit which is connected to the exhaust gas tube and oxidizes the exhaust gas by discharging electricity, irradiating ultraviolet rays or injecting an oxidizing agent; and a cleaning water discharge tube which discharges the cleaning water from the scrubber.

Here, the contaminant reducing device further includes a purification unit which is connected to the exhaust gas tube or the scrubber and electrolyzes seawater to generate hydrogen and an oxidizing agent for oxidizing nitrogen-based oxides or a neutralizing agent for neutralizing acidified cleaning water; and a fuel cell module which receives the hydrogen from he purification unit and generates electricity. The fuel cell module may supply electricity to the purification unit. The cleaning water supply tube branches from a seawater supply tube which receives seawater from the outside, and the contaminant reducing device further includes a pump which is installed on the seawater supply tube to pressurize the seawater, wherein the fuel cell module may supply electricity to the pump. The contaminant reducing device may further include an electrolyte tank which is installed on a seawater inlet tube connected to the purification unit and supplies an electrolyte to seawater.

The contaminant reducing device may further include a pretreatment unit which is connected to the exhaust gas tube and located in front of the oxidation unit to remove fine dust from the exhaust gas. The cleaning water supply tube branches from a seawater supply tube which receives seawater from the outside, the seawater supply tube supplies the seawater to the pretreatment unit, and the supplied seawater may be sprayed within the pretreatment unit. The contaminant reducing device further includes a fresh water supply tube which is connected to the cleaning water supply tube to supply fresh water, wherein the fresh water supply tube supplies the fresh water to the pretreatment unit, and the supplied fresh water may be sprayed within the pretreatment unit. The contaminant reducing device may further include a collecting tube which supplies the seawater or the fresh water that has passed through the pretreatment unit to the cleaning water supply tube. The pretreatment unit includes a centrifuge which separates the fine dust from the exhaust gas supplied through the exhaust gas tube, wherein the centrifuge may be a cyclone solid separator which receives the exhaust gas in a tangential direction.

The contaminant reducing device may further include a liquid catalyst injection unit which is connected to the exhaust gas tube behind the oxidation unit or to the cleaning water supply tube and maintains the exhaust gas in an oxidized state by injecting a liquid catalyst. The liquid catalyst may be organic sulfoxides obtained by oxidizing organic sulfides contained in oil.

The contaminant reducing device may further include a separation unit which is connected to the cleaning water discharge tube and separates the liquid catalyst from the cleaning water using a difference in specific gravity between the liquid catalyst and the cleaning water; and a circulation line which connects the separation unit and the liquid catalyst injection unit and circulates the liquid catalyst separated from the cleaning water by the separation unit to the liquid catalyst injection unit. The contaminant reducing device may further include a neutralizing agent supply unit which is connected to the scrubber and supplies a neutralizing agent. The contaminant reducing device may further include a pretreatment unit which is connected to the exhaust gas tube located in front of the oxidation unit and removes the fine dust from the exhaust gas.

Advantageous Effects

According to embodiments of a contaminant reducing device of the inventive concept, nitrogen monoxide contained in exhaust gas is oxidized with an oxidizing agent generated in a purification unit for electrolyzing seawater, and, at the same time, acidified cleaning water is neutralized with a neutralizing agent generated in the same purification unit. This cannot only reduce the system installation and maintenance cost but also can increase the utilization of space in a ship.

In addition, hydrogen generated by the electrolysis of seawater in the purification unit is supplied to a fuel cell module to generate electricity, and the generated electricity is used as a driving source of the purification unit and other devices. Therefore, the system can be operated more efficiently.

Further, according to embodiments of the contaminant reducing device of the inventive concept, since fine dust is removed before sulfur oxides and nitrogen oxides are oxidized, the oxidation efficiency can be improved. In addition, since the oxidized exhaust gas is double purified as it passes through a wet scrubber, contaminants contained in the exhaust gas can be significantly reduced. Also, the oxidized exhaust gas is dissolved in cleaning water to produce strong acid that can kill microorganisms in the cleaning water.

Moreover, according to embodiments of the contaminant reducing device of the inventive concept, the reduction of oxidized sulfur oxides and nitrogen oxides can be prevented by injecting a liquid catalyst into the oxidized sulfur oxides and nitrogen oxides before a gas-liquid contact. Therefore, the reduction effect of the sulfur oxides and the nitrogen oxides can be improved. In addition, since the oxidized exhaust gas is double purified as it passes through the wet scrubber, contaminants in the exhaust gas can be significantly reduced.

DETAILED DESCRIPTION

Description of Apparatus

Figure 1:
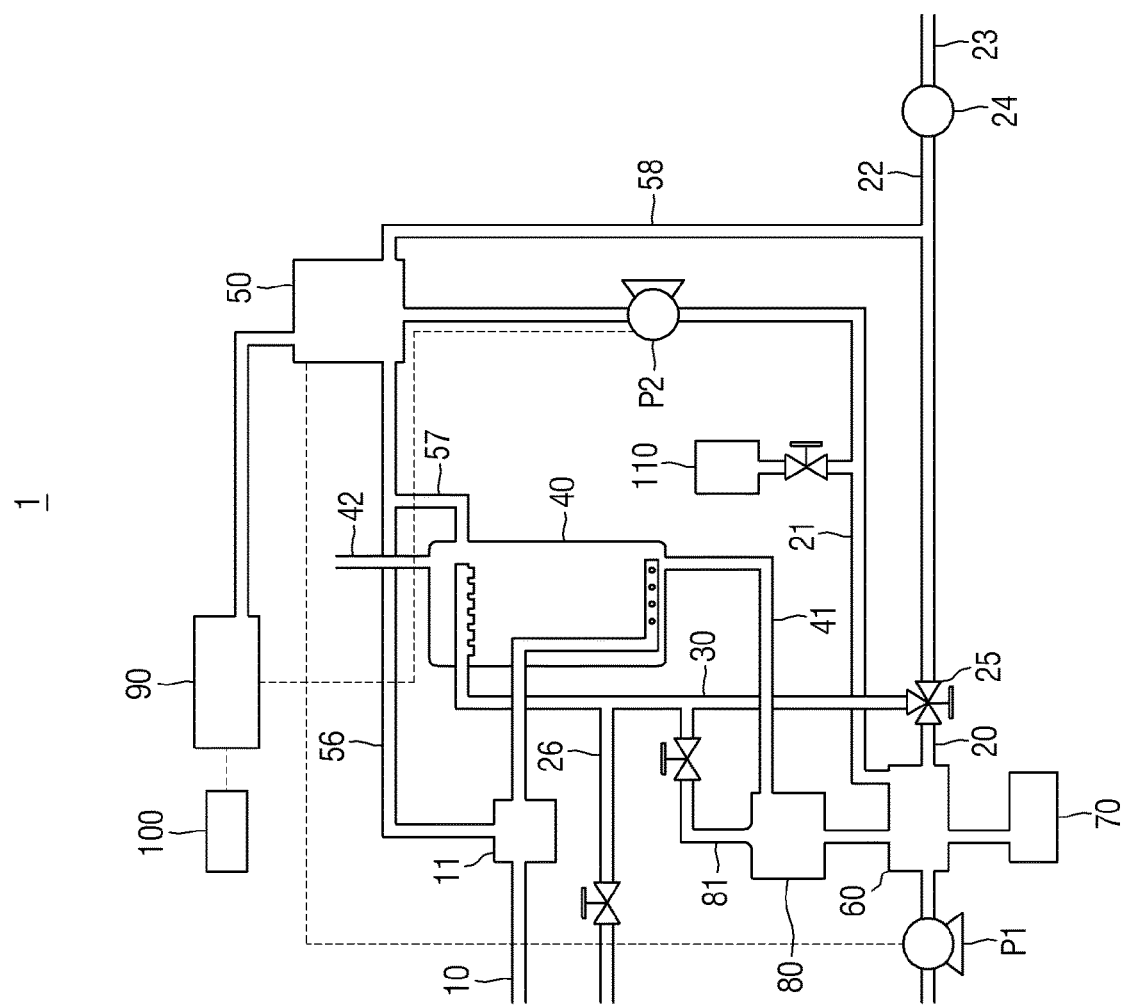
FIG. 1 is a schematic view of a contaminant reducing device according to a first embodiment of the inventive concept.

Advantages and features of the present inventive concept and methods of accomplishing the same may be understood more readily by reference to the following detailed description of exemplary embodiments and the accompanying drawings. The inventive concept may, however, be embodied in many different forms and should not be construed as being limited to the embodiments set forth herein. Rather, these embodiments are provided so that this disclosure will be thorough and complete and will fully convey the concept of the invention to those skilled in the art, and the inventive concept will only be defined by the appended claims. Like reference numerals refer to like elements throughout the specification.

Hereinafter, a contaminant reducing device according to a first embodiment of the inventive concept will be described in detail with reference to FIGS. 1 through 5.

A contaminant reducing device according to an embodiment of the inventive concept a device capable of reducing the concentration of various contaminants (nitrogen oxides, sulfur oxides, dust, etc.) contained exhaust gas to discharge that meets exhaust standards while treating cleaning water used to reduce the concentration of exhaust gas. The contaminant reducing device is mainly mounted on a ship to remove contaminants of exhaust gas generated in the ship.

The contaminant reducing device oxidizes nitrogen monoxide contained in exhaust gas with an oxidizing agent generated in a purification unit for electrolyzing seawater and, at the same time, neutralizes acidified cleaning water with a neutralizing agent generated in the same purification unit, thereby reducing the system installation and maintenance cost and increasing the utilization of space in the ship. In addition, the contaminant reducing device supplies hydrogen generated by the electrolysis of seawater in the purification unit to a fuel cell module to generate electricity and uses the generated electricity as a driving source of the purification unit and other devices. Therefore, the system can be operated more efficiently.

Figure 2:
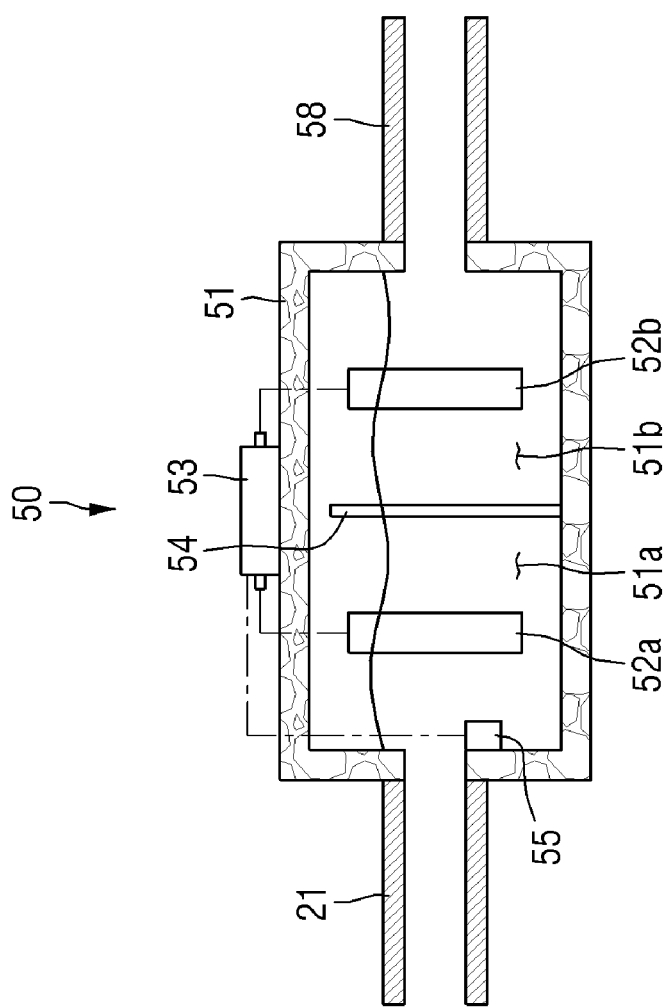
FIG. 2 is a cross-sectional view of an example of a purification unit of FIG. 1.
Figure 3:
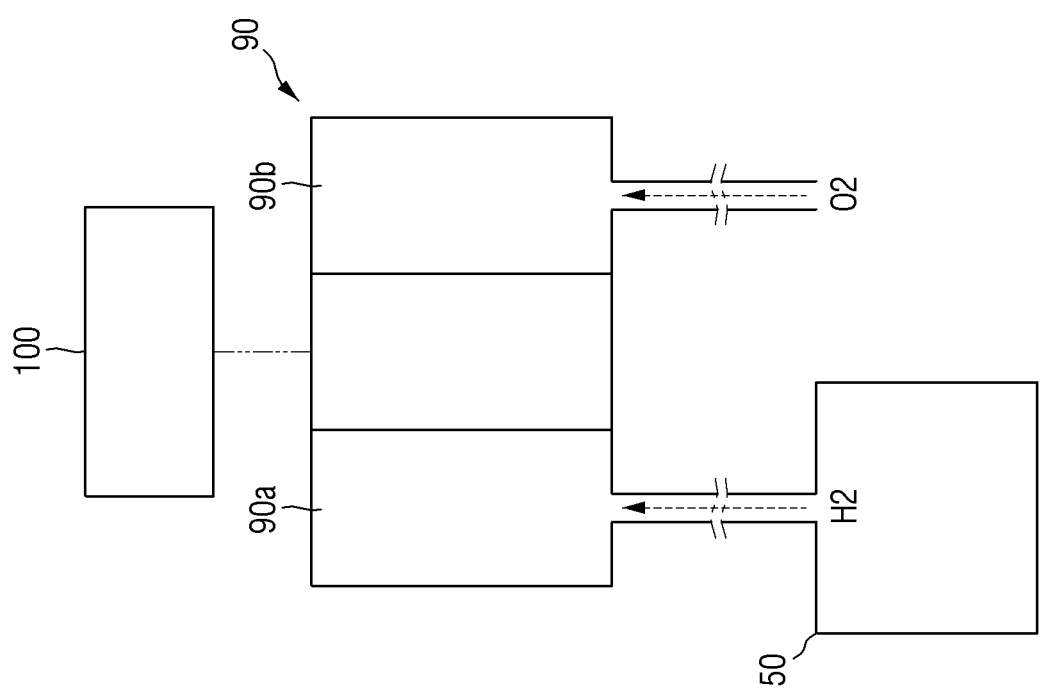
FIG. 3 is a cross-sectional view of an example of a fuel cell module of FIG. 1.

FIG. 1 is a schematic view of a contaminant reducing device according to a first embodiment of the inventive concept. FIG. 2 is a cross-sectional view of an example of a purification unit of FIG. 1. FIG. 3 is a cross-sectional view of an example of a fuel cell module of FIG. 1.

Referring to FIGS. 1 through 3, the contaminant reducing device 1 according to the first embodiment of the inventive concept includes an exhaust gas tube 10, a seawater supply tube 20, a cleaning water supply tube 30, a scrubber 40, the purification unit 50, the fuel cell module 90, and a cleaning water discharge tube 41.

The exhaust gas tube 10 is a tube through which exhaust gas moves from a combustion engine (not illustrated) and is connected to the scrubber 40 which will be described later. The exhaust gas tube 10 may be directly connected to an exhaust tube of the combustion engine and serve as a passage through which hot exhaust gas moves or waste gas remaining after most of the exhaust heat is recycled by various heat exchangers moves. Here, the combustion engine is a device that generates various power required for a ship by burning fuel. The combustion engine may be formed as, for example, a main engine, a generator engine, etc. The exhaust gas tube 10 may be connected to exhaust tubes of a plurality of combustion engines, and the combustion engines may selectively operate as needed. Since the combustion engines normally generate power by burning fossil fuel, they generate exhaust gas due to the combustion of the fossil fuel. The generated exhaust gas contains a large amount of sulfur oxides, nitrogen oxides and dust and is supplied to the scrubber 40 through the exhaust gas tube 10 connected to a side of each of the combustion engines.

The seawater supply tube 20 is a tube through which seawater is supplied from the outside, and at least one pump P1 for pressurizing seawater is installed on the seawater supply tube 20 to smoothly supply seawater to the scrubber 40. However, the seawater supply tube 20 supplies seawater not just to the scrubber 40 but can also supply seawater to a ballast water tank (not illustrated) if necessary.

The cleaning water supply tube 30 may branch from a side of the seawater supply tube 20 and may be connected to the scrubber 40. A first control valve 25 may be installed at a connection portion between the seawater supply tube 20 and the cleaning water supply tube 30. The first control valve 25 may be formed as a three-way valve to control the amount of seawater supplied through the cleaning water supply tube 30 or adjust a ratio of seawater supplied to the cleaning water supply tube 30 to seawater flowing through the seawater supply tube 20. The seawater supply tube 20 is sequentially connected to a mixing tube 22 and a seawater discharge tube 23 located behind the cleaning water supply tube 30. The seawater that has been electrolyzed by the purification unit 50 which will be described later may flow through the mixing tube 22 and may be discharged to the outside through the seawater discharge tube 23.

The cleaning water supply tube 30 is a tube for supplying the scrubber 40 with cleaning water which is at least one of seawater, fresh water, and a mixture of seawater and fresh water. An end of the cleaning water supply tube 30 may be connected to the seawater supply tube 20 or a fresh water supply tube 26, and the other end of the cleaning water supply tube 30 may be connected to the scrubber 40. That is, the cleaning water supply tube 30 can selectively receive seawater and fresh water. Based on the assumption that the cleaning water is limited to seawater, a process in which seawater is mainly supplied to the scrubber 40 through the cleaning water supply tube 30 will be described in more detail below.

The seawater introduced from the outside through the seawater supply tube 20 is supplied to the scrubber 40 via the cleaning water supply tube 30. The scrubber 40 is a device for spraying cleaning water supplied through the cleaning water supply tube 30 to exhaust gas introduced through the exhaust gas tube 10 in order to bring the exhaust gas and the cleaning water into contact with each other. The scrubber 40 may be a typical wet scrubber. Here, an end of the cleaning water supply tube 30 which is disposed inside the scrubber 40 may be located in an upper part of the scrubber 40 and may branch into a plurality of parts to spray the cleaning water in the form of fine particles. That is, the cleaning water supply tube 30 disposed in the upper part of the scrubber 40 sprays the cleaning water toward a lower part of the scrubber 40 where the exhaust gas tube 20 is located, thereby effectively bringing the exhaust gas and the cleaning water into contact with each other. As the exhaust gas and the cleaning water come into contact with each other within the scrubber 40, contaminants such as nitrogen oxides, sulfur oxides and dust contained in exhaust gas may be removed. The exhaust gas from which the contaminants is such as the nitrogen oxides, the sulfur oxides and the dust have been removed may be discharged to the outside through a discharge tube 42. Since the exhaust gas discharged through the discharge tube 42 is without the contaminants such as the nitrogen oxides, the sulfur oxides and the dust, it meets the exhaust standards and thus can be discharged to the atmosphere as it is.

The cleaning water, which has absorbed the nitrogen oxides, the sulfur oxides and the dust through the contact with the contaminant-containing exhaust gas in the scrubber 40, is discharged out of the scrubber 40 through the cleaning water discharge tube 41.

The purification unit 50 electrolyzes seawater to generate hydrogen and an oxidizing agent for oxidizing nitrogen-based oxides or a neutralizing agent for neutralizing acidified cleaning water. The purification unit 50 may be connected to the exhaust gas tube 10, the seawater supply tube 20, or the scrubber 40. In other words, the purification unit 50 may supply the oxidizing agent or the neutralizing agent to the exhaust gas tube 10, the seawater supply tube 20, or the scrubber 40. In addition, the purification unit 50 may generate a sterilizing agent by electrolyzing seawater. The generated sterilizing agent may be supplied to the scrubber 40 and the seawater supply tube 20 through a second injection tube 57 and a third injection tube 58 to kill microorganisms present in seawater. Then, the sterilized seawater is checked for excess oxidizing agent by a sensor unit 24 before being discharged to the sea through the seawater discharge tube 23. Here, if the amount of oxidizing agent contained in the seawater is excessive, sodium thiosulfate ($Na_2S_2O_3$) is added to reduce the amount of oxidizing agent. After that, the seawater is discharged to the sea.

The purification unit 50 includes an electrolytic bath 51, a positive electrode plate 52a, a negative electrode plate 52b, and a rectifier 53.

Referring to FIG. 2, the electrolytic bath 51 is a container or chamber having a receiving space therein, and seawater supplied through the seawater supply tube 20 is accommodated in the electrolytic bath 51. A side of the electrolytic bath 51 is connected to a seawater inlet tube 21, which branches from the seawater supply tube 20, so as to receive seawater. At least one pump P2 may be installed on the seawater inlet tube 21 to smoothly supply seawater to the electrolytic bath 51. The positive, electrode plate 52a and the negative electrode plate 52b are installed in the electrolytic bath 51.

The positive electrode plate 52a and the negative electrode plate 52b are arranged in the electrolytic bath 51 in the flow direction of seawater and are separated from each other by a predetermined distance to face each other. A barrier 54 made of a hydrophilic porous membrane is installed between the positive electrode plate 52a and the negative electrode plate 52b to divide the inside of the electrolytic bath 51 into a first area 51a in which the positive electrode plate 52a is located and a second area 51b in which the negative electrode plate 52b is located. However, the barrier 54 is not necessarily made of a hydrophilic porous membrane. The barrier 54 can also be deformed into membranes having various structures or can be omitted if necessary. Each of the positive electrode plate 52a and the negative electrode plate 52b is electrically connected to the rectifier 53 by a cable.

The rectifier 53 supplies a rectified current to each of the positive electrode plate 52a and the negative electrode plate 52b. In the drawing, the rectifier 53 is installed outside the electrolytic bath 51. However, the rectifier 53 is not necessarily installed outside the electrolytic bath 51. For example, the rectifier 53 can be installed inside the electrolytic bath 51.

In the electrolytic bath 51, sodium chloride (NaCl)) contained in seawater is electrolyzed by a current supplied from the rectifier 53. Accordingly, an oxidation reaction occurs in the positive electrode plate 52a to produce a chlorine gas ($Cl_2$), and a hydrogen gas ($H_2$) and a hydroxyl group ($OH^-$) are produced in the negative electrode plate 52b. At this time, the chlorine gas ($Cl_2$) and the hydroxyl group ($OH^-$) chemically react with each other to produce sodium hypochlorite (NaOCl) and hypochlorous acid (HOCl) having strong oxidizing power. A concentration measuring sensor 55 is provided inside the electrolytic bath 51 to measure the concentration of the oxidizing agent, the sterilizing agent or the neutralizing agent generated. Therefore, the rectifier 53 can adjust the intensity of the current supplied based on the concentration value measured by the concentration measuring sensor 55.

Specifically, the following reaction occurs in the positive electrode plate 52a:

$$2H_2O \rightarrow O_2 + 4H^+ + 4e^-$$

$$2Cl^- \rightarrow Cl_2 + 2e^-$$

In addition, the following reaction occurs in the negative electrode plate 52b:

$$2H_2O + 2e^- \rightarrow H_2 + 2OH^-$$

$$2Na^+ + 2e^- \rightarrow 2Na$$

$$Na + H_2O \rightarrow NaOH.$$

In conclusion, $$Cl_2 + 2OH^- \rightarrow OCl^- + Cl^- + H_2O$$

$$Na^+ + OCl^- \rightarrow NaOCl$$

$$NaOCl + H_2O \rightarrow HOCl$$

That is, the oxidizing agent may be sodium hypochlorite (NaOCl) or hypochlorous acid (HOCl) produced by the electrolysis of seawater, and the purification unit 50 may atomize the oxidizing agent into a liquid phase and inject the atomized oxidizing agent into the exhaust gas tube 10 through a first injection tube 56. Specifically, the purification unit 50 may oxidize nitrogen monoxide contained in exhaust gas into nitrogen dioxide by injecting the oxidizing agent into the exhaust gas tube 10 through the first injection tube 56. The nitrogen dioxide is easily dissolved in water as compared with the nitrogen monoxide. Therefore, the nitrogen dioxide can be easily dissolved and removed in the cleaning water in the scrubber 40. The first injection tube 56 may atomize the liquid oxidizing agent and inject the atomized liquid oxidizing agent into the exhaust gas tube 10 or may spray the liquid oxidizing agent to the exhaust gas through an oxidation unit 11 installed on the exhaust gas tube 10. The oxidation unit 11 may atomize, dropletize, or vaporize the liquid oxidizing agent using a nozzle, an ultrasonic vibrator, a spray, a heating plate, or the like.

In addition, the neutralizing agent may be sodium hypochlorite (NaOCl) produced by the electrolysis of seawater or may be a diluent of the sodium hypochlorite (NaOCl), and the purification unit 50 may inject the neutralizing agent into the scrubber 40 through the second injection tube 57. Specifically, the neutralizing can neutralize the cleaning water acidified by the reaction of nitrogen oxides (NOx) and sulfur oxides (SOx) with the cleaning water. Since the nitrogen oxides (NOx) and the sulfur oxides (SOx) react with seawater to produce nitric acid ($HNO_3$) and sulfuric acid ($H_2SO_4$), respectively, the purification unit 50 may neutralize the acidified cleaning water by injecting sodium hypochlorite (NaOCl) into the scrubber 40. The following reaction occurs in the scrubber 40:

$$2NaOCl + 2HNO_3 \rightarrow 2NaNO_3 + 2HOCl$$

$$2NaOCl + H_2SO_4 \rightarrow Na_2SO_4 + 2HOCl$$

The sodium hypochlorite (NaOCl) reacts with the nitric acid ($HNO_3$) and the sulfuric acid ($H_2SO_4$) to additionally produce hypochlorous acid (HOCl). Therefore, microorganisms present in the cleaning water can be killed. Here, since the hypochlorous acid (HOCl) is weakly acidic, a neutralizing agent such as sodium thiosulfate ($Na_2S_2O_3$) or sodium hydroxide (NaOH) can be added.

The purification unit 50 may kill microorganisms present in seawater to be discharged to the sea through the mixing tube 22 and the seawater discharge tube 23 by injecting the sterilizing agent into the seawater supply tube 20 through the third injection tube 58. The purification unit 50 may also inject the neutralizing agent (NaOH) directly into the scrubber 40 through the second injection tube 57. If the cleaning water is not sufficiently neutralized by the neutralizing agent supplied from the purification unit 50, a neutralizing agent injection unit (not illustrated) may be added to additionally neutralize the cleaning water.

The hydrogen produced by the electrolysis of seawater has very low solubility in water (hydrogen solubility: 0.0016 g/kg). Therefore, the hydrogen can be easily separated from water by a gas-liquid separator (not illustrated) and then supplied to the fuel cell module 90. The fuel cell module 90 may receive oxygen and the hydrogen supplied from the purification unit 50 to generate electricity. For example, the fuel cell module 90 may be formed as a polymer electrolyte fuel cell that is operated at a low temperature of about 50° C. to about 200° C. and is suitable for small capacity output. The polymer electrolyte fuel cell is a fuel cell that uses a polymer membrane with hydrogen ion exchange properties as an electrolyte. The polymer electrolyte fuel cell has advantages of high power generation efficiency, high output density, and fast response to load changes. However, the fuel cell module 90 is not limited to the polymer electrolyte fuel cell and can be modified into various fuel cells that operate at a low temperature. For example, the fuel cell module 90 may also be formed as a phosphoric acid fuel cell.

The fuel cell module 90 generates electricity by receiving oxygen-containing air and hydrogen. Here, the air is not limited to general air generally composed of about 80% of nitrogen and about 20% of oxygen which can be obtained in a natural state. The concentration of oxygen in the air may be higher or lower than that of oxygen in the general air, and the composition of the air may be different from that of the general air. That is, the air may collectively refer to gases containing oxygen required in the fuel cell module 90.

Referring to FIG. 3, an anode 90a and a cathode 90b may be formed in the fuel cell module 90. The anode 90a may receive hydrogen from the purification unit 50 and may be formed at a side of the fuel cell module 90. The cathode 90*b* may receive oxygen, oxygen-containing air or oxygen-containing exhaust gas and may be formed at the other side of the fuel cell module 90. The hydrogen supplied to the anode 90*a* and the oxygen supplied to the cathode 90*b* may chemically react with each other to generate electricity, and a reaction formula of the hydrogen and the oxygen is as follows:

Anode: $H_2 \rightarrow 2H^+ + 2e^-$

Cathode: $0.5O_2 + 2H^+ + 2e^- \rightarrow H_2O$

Total: $H_2 + 0.5O_2 \rightarrow H_2O + \text{current} + \text{heat}$

In the anode 90*a*, the electrical oxidation of the hydrogen ($H_2$), which is a fuel, occurs, and hydrogen ions ($2H^+$) and electrons ($2e^-$) move to the cathode 90*b*. The hydrogen ions ($2H^+$) move from the anode 90*a* to the cathode 90*b* via a polymer membrane located between the anode 90*a* and the cathode 90*b*, and the electrons ($2e^-$) move from the anode 90*a* to the cathode 90*b* via an electric circuit that connects the anode 90*a* and the cathode 90*b* to the outside. In the cathode 90*b*, the electrochemical reduction of the oxygen ($O_2$), which is an oxidizing agent, occurs, and the oxygen ($O_2$) finally reacts with the hydrogen ions ($2H^+$) and the electrons ($2e^-$) to change into water ($H_2O$). At the same time, direct current (DC) power is generated, as well as heat. The generated DC power can be used as the power of a DC motor or can be converted into alternating current (AC) power by an inverter.

The electricity generated through the above process may supplied to the purification unit 50, the pump P1 installed on the seawater supply tube 20 and the pump P2 installed on the seawater inlet tube 21 and used as a power source of each of the purification unit 50, the pump P1 and the pump P2 or as a power source of other facilities, When the electricity generated by the fuel cell module 90 is supplied to the purification unit 50, it may be used as part of a power source necessary for electrolyzing seawater.

A battery module 100 for storing generated electricity may be provided on a side of the fuel cell module 90. The electricity stored in the battery module 100 may be supplied to various places as needed.

An electrolyte tank 110 for supplying an electrolyte to seawater may be provided on the seawater supply tube 20 or the seawater inlet tube 21 branching from the seawater supply tube 20. Here, the electrolyte may be sodium chloride (NaCl). Ships sail in the waters around the world, and the concentration of salt contained in seawater may vary depending on the area of sea. In particular, when the salt concentration in seawater is too low, electrolysis does not occur smoothly in the purification unit 50. Thus, an oxidizing or neutralizing agent with appropriate concentration is not generated. Consequently, exhaust gas may fail to meet emission standards. However, the electrolyte tank 110 provided on the seawater supply tube 20 or the seawater inlet tube 21 to supply an electrolyte can facilitate electrolysis in the purification unit 50 even when seawater containing a small amount of sodium chloride is supplied to the purification unit 50. Accordingly, an oxidizing agent or a neutralizing agent can be easily generated.

The cleaning water discharge tube 41 is a tube for discharging cleaning water from the scrubber 40 and may be connected back to the seawater supply tube 20 by a filter unit 60. That is, the cleaning water discharge tube 41 may separate solid-phase particles from the cleaning water using the filter unit 60 and then discharge the cleaning water to the outside. The cleaning water discharge tube 41 is not necessarily connected to the seawater supply tube 20 and can also be independently connected to the outside of the ship.

A circulation tube 81 may be connected to the cleaning water discharge tube 41. The circulation tube 81 is a tube for recirculating the cleaning water discharged through the cleaning water discharge tube 41 to the cleaning water supply tube 30. When there is no need to discharge the cleaning water to the outside, the cleaning water may be circulated to the scrubber 40 and reused.

A recirculation tank 80 may be installed between the cleaning water discharge tube 41 and the circulation tube 81. The recirculation tank 80 may store some of the cleaning water discharged from the scrubber 40 and may serve as a kind of buffer tank that allows a certain amount of cleaning water to be circulated through the circulation tube 81.

The recirculation tank 80 may include any one of a centrifuge, a gravity separator and a filter to remove solid-phase particles from the cleaning water and to recirculate the cleaning water through the circulation tube 81.

Since the cleaning water supply tube 30 is connected to the seawater supply tube 20, the fresh water supply tube 26 and the circulation tube 81, it can appropriately mix seawater, fresh water and circulating water in view of the concentration of the exhaust gas, the treatment capacity of the scrubber 40, the concentration and degree of contamination of the cleaning water, etc. and supply the mixture to the scrubber 40.

The filter unit 60 is installed behind the scrubber 40 to separate solid-phase particles from the cleaning water discharged from the scrubber 40. Like the recirculation tank 80, the filter unit 60 may separate solid-phase particles from the cleaning water using at least one of a centrifuge, a gravity separator and a filter and discharge the solid-phase particles to a sludge tank 70. The filter unit 60 may be connected to the seawater supply tube 20 between the pump P1 and the first control valve 25. That is, the seawater supplied from the seawater supply tube 20 may pass through the filter unit 60 and then may be supplied to the scrubber 40 through the cleaning water supply tube 30, and the cleaning water that has passed through the scrubber 40 may pass through the filter unit 60 again. That is, both the seawater introduced from the outside and the cleaning water that has passed through the scrubber 40 can be filtered by one filter unit 60. In addition, one or two filter units 60 can be used commonly or independently to remove materials having larges particles from the cleaning water that has passed through the cleaning water discharge tube 41 or the seawater that has passed through the seawater supply tube 20.

The neutralizing agent or the sterilizing agent may be sprayed to the cleaning water or the seawater, which has passed through the filter unit 60, through the third injection tube 58. The mixing tube 22 to which a mixture of the seawater and the cleaning water is discharged may be installed between the filter unit 60 and the seawater discharge tube 23, and the third injection tube 58 may be connected to the seawater supply tube 20 or the mixing tube 22. The sensor unit 24 may be installed on the seawater discharge tube 23 to identify, in real time, at least one of total residual oxidant, pH value, and microbial concentration of the cleaning water and the seawater to be discharged. The sensor unit 24 may be, for example, a total residual oxidant sensor, and the purification unit 50 may adjust the supply of the oxidizing agent, the neutralizing agent and the sterilizing agent according to the result value of the sensor unit 24.

The cleaning water and the seawater discharged through the mixing tube 22 are discharged to the outside through the seawater discharge tube 23.

The operation of the contaminant reducing device 1 will now be described in more detail with reference to FIGS. 4 and 5.

Figure 4:
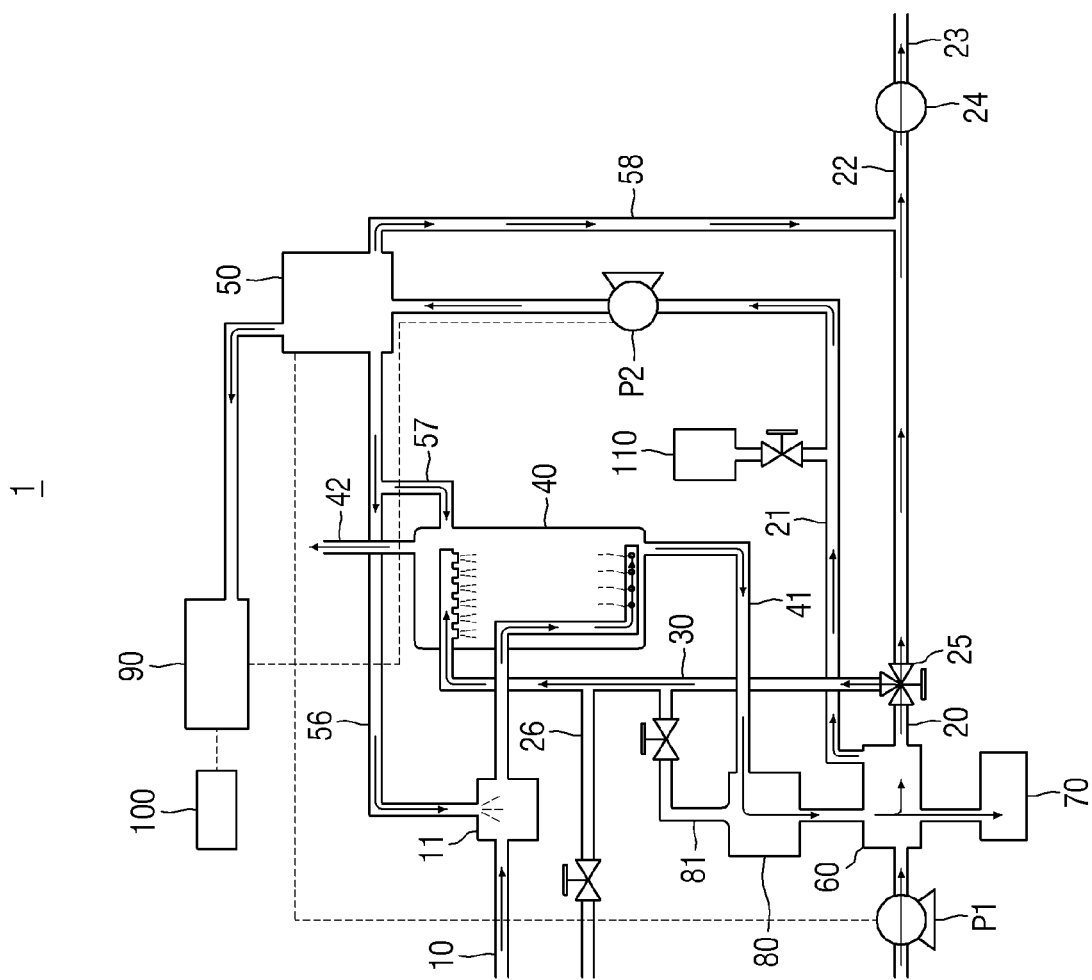
FIGS. 4 and 5 illustrate the operation of the contaminant reducing device of FIG. 1.
Figure 5:
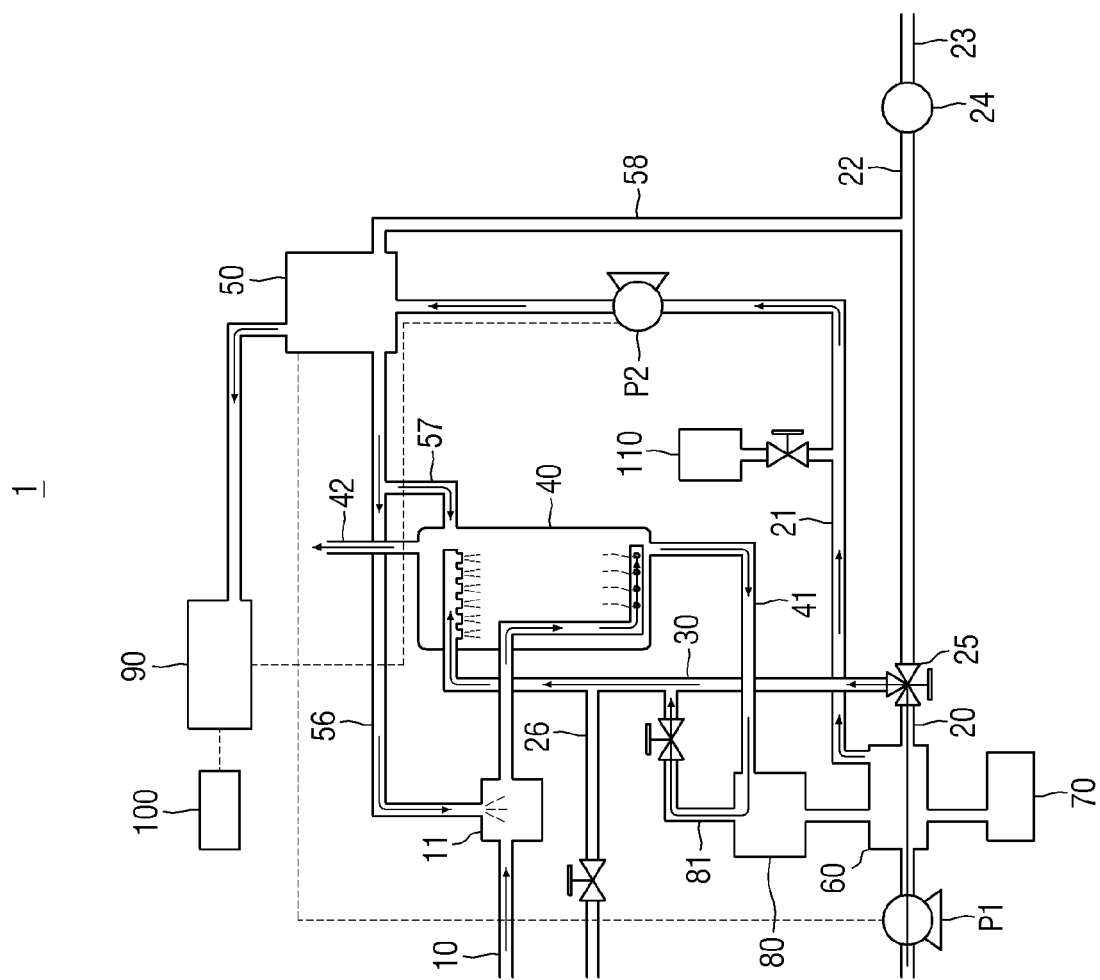

FIGS. 4 and 5 illustrate the operation of the contaminant reducing device of FIG. 1. Specifically, FIG. 4 illustrates an open loop mode in which seawater supplied to the seawater supply tube is directly discharged to the outside after passing through the scrubber, and FIG. 5 illustrates a closed loop mode in which seawater supplied to the seawater supply tube is recirculated through the circulation tube after passing through the scrubber.

Referring to FIG. 4, some of the seawater introduced through the seawater supply tube 20 is supplied to the scrubber 40 through the cleaning water supply tube 30, and the rest of the seawater is supplied to the purification unit 20 through the seawater inlet tube 21. Cleaning water may be sprayed from the upper part of the scrubber 40 and fill the lower part of the scrubber 40 to a certain level. At this time, exhaust gas supplied through the exhaust gas tube 10 may be sprayed from the lower part of the scrubber 40.

The purification unit 50 may oxidize nitrogen monoxide of the exhaust gas into nitrogen dioxide by spraying an oxidizing agent generated by the electrolysis of seawater before the exhaust gas is supplied to the scrubber 40. The purification unit 50 may also spray a neutralizing agent to the exhaust gas tube 10 or the scrubber 40 in view of the pH value of the cleaning water.

Since the exhaust gas can be sprayed within the cleaning water filling the lower part of the scrubber 40, contaminants such as nitrogen oxides, sulfur oxides and dust can be removed. In addition, the contaminants can be removed again by the cleaning water sprayed from the upper part of the scrubber 40. Through this process, the contaminants contained in the exhaust gas are removed, and the exhaust gas from which the contaminants have been removed is discharged to the outside through the discharge tube 42.

The cleaning water that has passed through the scrubber 40 contains contaminants such as nitrogen oxides, sulfur oxides and dust and moves to the filter unit 60 through the cleaning water discharge tube 41. The filter unit 60 separates contaminants such as solid-phase particles from the cleaning water and stores the separated contaminants in the sludge tank 70. The cleaning water without the contaminants is discharged to the outside through the seawater discharge tube 23. Here, if the total residual oxidant and pH value (measured by the sensor unit 24) of the cleaning water passing through the seawater discharge tube 23 are outside a reference range, they are adjusted to be within the reference range by injecting (not illustrated) sodium thiosulfate ($Na_2S_2O_3$) into the mixing tube 22 or injecting the neutralizing agent produced in the purification unit 50 into the scrubber 40 through the second injection tube 57. Then, the cleaning water is discharged to the outside.

Hydrogen generated by the electrolysis of seawater in the purification unit 50 may be supplied to the fuel cell module 90, and electricity generated by the fuel cell module 90 may be used as a power source of the purification unit 50 or the pumps P1 and P2 or may be stored in the battery module 100.

When seawater containing a small amount of sodium chloride is introduced through the seawater supply tube 20, the electrolyte tank 110 may supply an electrolyte to the seawater flowing through the seawater inlet tube 21.

Referring to FIG. 5, some of the seawater introduced through the seawater supply tube 20 is supplied to the scrubber 40, and some of the seawater is supplied to the purification unit 50. Cleaning water discharged to the cleaning water discharge tube 41 via the scrubber 40 is temporarily stored in the recirculation tank 80 and then circulated back to the cleaning water supply tube 30 through the circulation tube 81. That is, the remaining process of FIG. 5 is substantially the same as that of FIG. 4, except that the cleaning water is recirculated through the circulation tube 81.

The seawater introduced through the seawater supply tube 20 is circulated sequentially through the cleaning water supply tube 30, the scrubber 40, the cleaning water discharge tube 41, the recirculation tank 80 and the circulation tube 81. The process of FIG. 4 and the process of FIG. 5 may be performed together in view of the degree of contamination, pH value, etc. of the seawater. The process of FIG. 5 may be used when the seawater cannot be discharged to the outside, for example, when the ship is passing through an area where the discharge of the seawater is restricted. If the cleaning water is highly contaminated due to the recirculation of the cleaning water, it may be discharged to the outside after solid-phase particles are removed from the cleaning water by the filter unit 60. Then, new seawater may be supplied again to the scrubber 40.

The process of FIG. 4 and the process of FIG. 5 can be selectively or sequentially used as needed.

Hereinafter, a contaminant reducing device according to a second embodiment of the inventive concept will be described in detail with reference to FIGS. 6 through 11.

The contaminant reducing device can improve oxidation efficiency by removing fine dust before oxidizing sulfur oxides and nitrogen oxides. In addition, since oxidized exhaust gas is double purified as it passes through a wet scrubber, contaminants in the exhaust gas can be significantly reduced. Also, the oxidized exhaust gas is dissolved in cleaning water to produce strong acid that can kill microorganisms in the cleaning water.

The contaminant reducing device will now be described in detail with reference to FIGS. 6 and 7.

Figure 6:
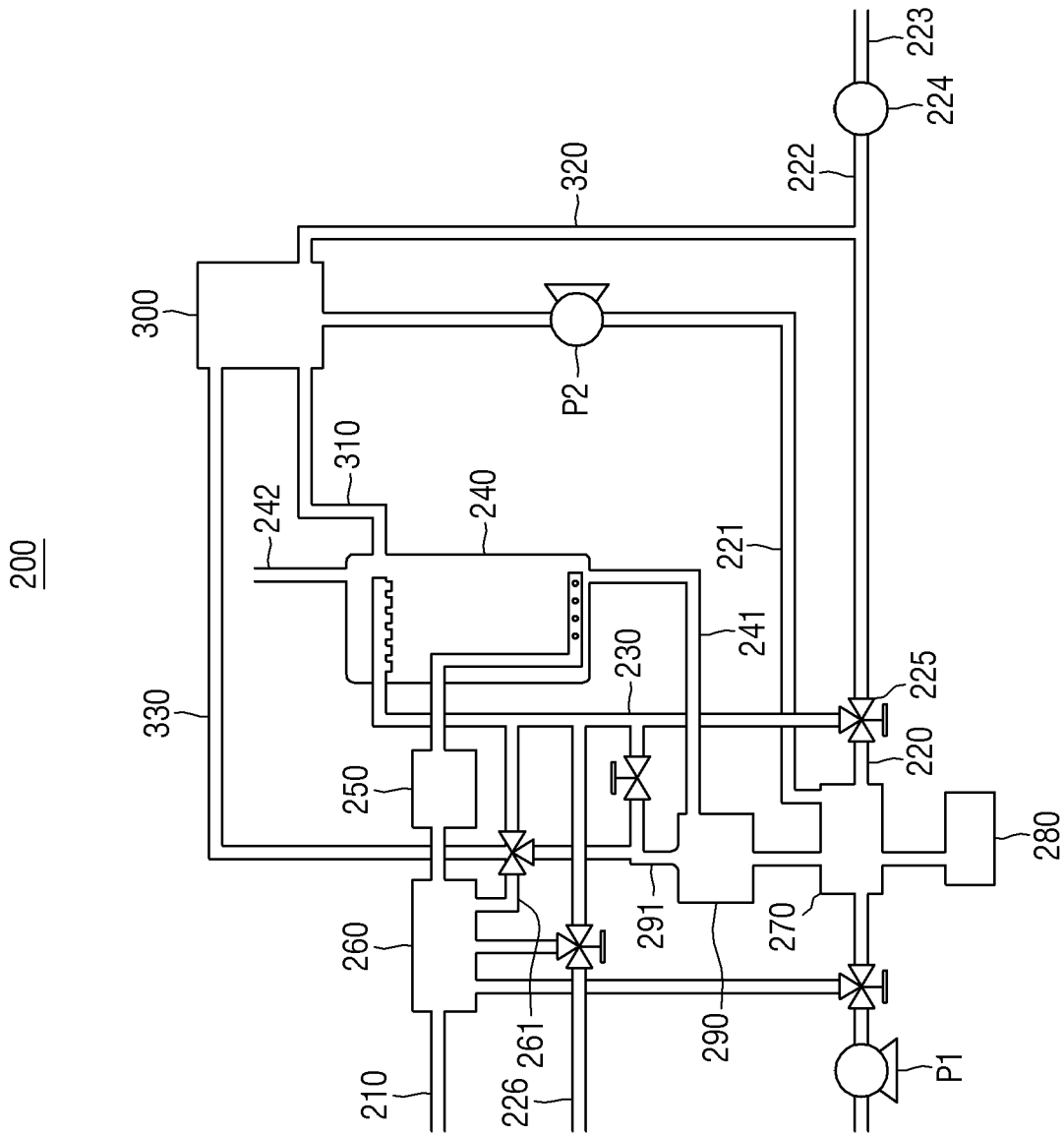
FIG. 6 is a schematic view of a contaminant reducing device according to a second embodiment of the inventive concept.
Figure 7:
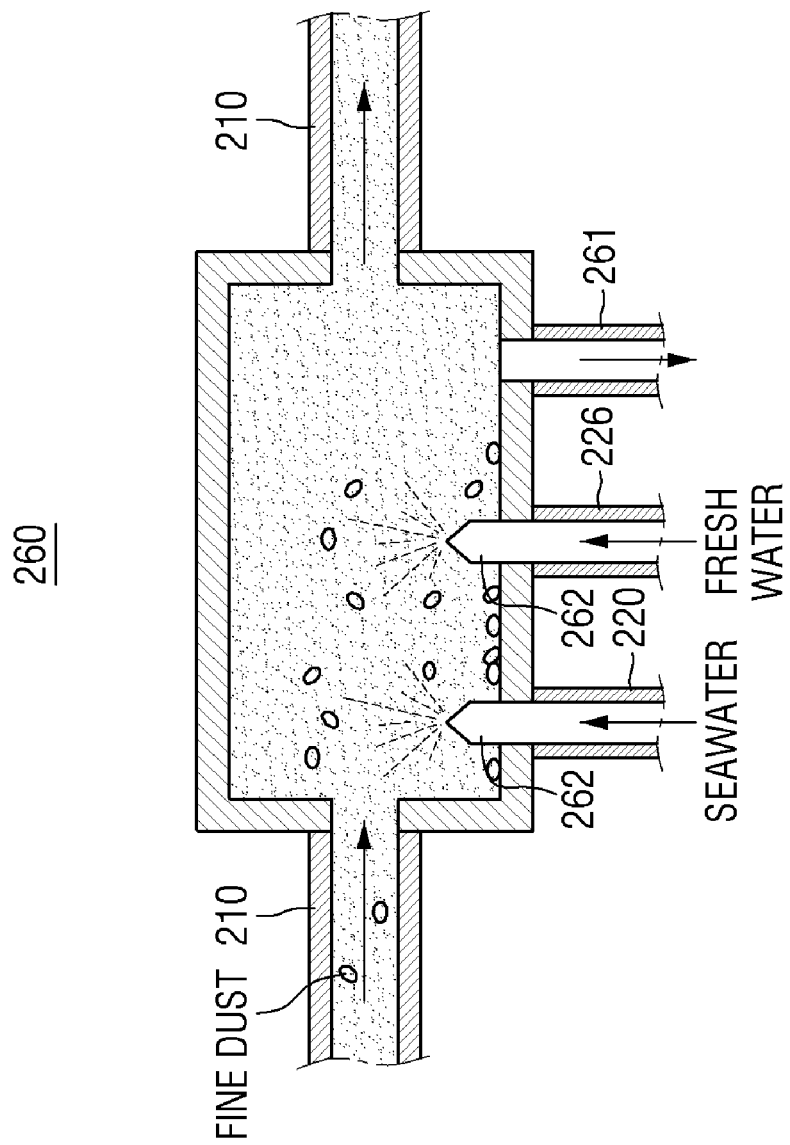
FIG. 7 is a cross-sectional view of an example of a pretreatment unit of FIG. 6.

FIG. 6 is a schematic view of a contaminant reducing device according to a second embodiment of the inventive concept. FIG. 7 is a cross-sectional view of an example of a pretreatment unit of FIG. 6.

The contaminant reducing device 200 according to the inventive concept includes an exhaust gas tube 210, a cleaning water supply tube 230, a scrubber 240, an oxidation unit 250, the pretreatment unit 260, a neutralizing agent supply unit 300, and a cleaning water discharge tube 241.

The exhaust gas tube 210 is a tube through which exhaust gas moves from a combustion engine (not illustrated) and is connected to the scrubber 240 which will be described later. The exhaust gas tube 210 may be directly connected to an be of the combustion engine and serve as a passage through which hot exhaust gas moves or waste gas remaining after most of the exhaust heat is recycled by various heat exchangers moves. The cleaning water supply tube 230 is a tube for supplying the scrubber 240 with cleaning water which is at least one of seawater, fresh water, and a mixture of seawater and fresh water. An end of the cleaning water supply tube 230 may be connected to a seawater supply tube 220 or a fresh water supply tube 226, and the other end of the cleaning water supply tube 230 may be connected to the scrubber 240. That is, the cleaning water supply tube 230 can selectively receive seawater and fresh water. Based on the assumption that the cleaning water is limited to seawater, a process in which seawater is mainly supplied to the scrubber 240 through the cleaning water supply tube 230 will be described in more detail below.

The seawater supply tube 220 is a tube through which seawater is supplied from the outside, and at least one pump P1 for pressurizing seawater is installed on the seawater supply tube 220 to smoothly supply seawater to the scrubber 240.

The cleaning water supply tube 230 may branch from a side of the seawater supply tube 220 and may be connected to the scrubber 240. A first control valve 225 may be installed at a connection portion between the seawater supply tube 220 and the cleaning water supply tube 230. The first control valve 225 may be formed as a three-way valve to control the amount of seawater supplied through the cleaning water supply tube 230 or adjust a ratio of seawater supplied to the cleaning water supply tube 230 to seawater flowing through the seawater supply tube 220. The seawater into which a neutralizing agent of the neutralizing agent supply unit 300 to be described later has been injected may flow through a mixing tube 222 and may be discharged to the outside through a seawater discharge tube 223.

The seawater introduced from the outside through the seawater supply tube 220 is supplied to the scrubber 240 via the cleaning ate supply tube 230. The scrubber 240 is a device for spraying cleaning water supplied through the cleaning water supply tube 230 to exhaust gas introduced through the exhaust gas tube 210 in order to bring the exhaust gas and the cleaning water into contact with each other. The scrubber 240 may be a wet scrubber. Here, an end of the cleaning water supply tube 230 which is disposed inside the scrubber 240 may be located in an upper part of the scrubber 240 and gray branch into a plurality of parts to spray the cleaning water in the form of fine particles. That is, the cleaning water supply tube 230 disposed in the upper part of the scrubber 240 sprays the cleaning water toward a lower part of the scrubber 240 where the exhaust gas tube 220 is located, thereby effectively bringing the exhaust gas and the cleaning water into contact with each other. As the exhaust gas and the cleaning water come into contact with each other within the scrubber 240, contaminants such as nitrogen oxides, sulfur oxides and dust contained in the exhaust gas may be removed. The exhaust gas from which the contaminants such as the nitrogen oxides, the sulfur oxides and the dust have been removed may be discharged to the outside through a discharge tube 242. Since the exhaust gas discharged through the discharge tube 242 is without the contaminants such as the nitrogen oxides, the sulfur oxides and the dust, it meets the exhaust standards and thus can be discharged to the atmosphere as it is.

The cleaning water, which has absorbed the nitrogen oxides, the sulfur oxides and the dust through the contact with the contaminant-containing exhaust gas in the scrubber 240, is discharged out of the scrubber 240 through the cleaning water discharge tube 241. Here, the nitrogen oxides and the sulfur oxides are dissolved in the cleaning water inside the scrubber 240 to form strongly acidic sulfuric acid ($H_2SO_4$) and nitric acid ($HNO_3$). Therefore, microorganisms contained in the cleaning water can be killed.

The exhaust gas supplied through the exhaust gas tube 210 has its fine dust removed by the pretreatment unit 260. The exhaust gas may first be purified by the oxidation unit 250 and then purified again by the scrubber 240.

The oxidation unit 250 is a device for oxidizing exhaust gas through pulsed corona discharge or irradiation of ultraviolet rays and may be connected to the exhaust gas tube 210. A structure in which the oxidation unit 250 oxidizes exhaust gas through pulsed corona discharge will now be described in more detail.

When corona discharge occurs in the oxidation unit 250 due to a pulsed high voltage, exhaust gas becomes a plasma state and produces ozone and oxidative radicals such as $O_2$ and OH to remove contaminants such as nitrogen oxides and sulfur oxides. In the oxidation unit 250, the exhaust gas may react according to the following reaction formula to oxidize contaminants contained in the exhaust gas, that is, sulfur oxides or nitrogen oxides.

<Reaction Formula>

$NO+O \rightarrow NO_2$ $NO+H_2O \rightarrow NO_2+OH^-$ $NO+OH^- \rightarrow HNO_2$ $HNO_2+OH^- \rightarrow NO_2+H_2O$ $NO+O_3 \rightarrow NO_2+O_2$ $NO_2+OH^- \rightarrow HNO_3$ $SO_2+OH^- \rightarrow HSO_3^-$ $HSO_3^-+OH^- \rightarrow H_2SO_4$ $SO_2+O \rightarrow SO_3^{2-}$ $SO_3^{2-}+H_2O \rightarrow H_2SO_4$ The pretreatment unit 260 is a device for removing fine dust contained in exhaust gas. The pretreatment unit 260 may be connected to the exhaust gas tube 210 and located in front of the oxidation unit 250. The pretreatment unit 260 may reduce the concentration of fine dust in exhaust gas by spraying water molecules to the fine dust, reduce the fine dust concentration by using a separation membrane having a low transmittance of fine dust, or reduce the fine dust concentration by using a cyclone centrifuge. A structure in which the pretreatment unit 260 reduces the concentration of fine dust in exhaust gas by spraying water molecules to the fine dust will now be described in more detail with reference to FIG. 7.

A side of the seawater supply tube 220 may branch off to he connected to the pretreatment unit 260 and may spray seawater introduced from the outside into the pretreatment unit 260. Here, since a nozzle unit 262 is coupled to an end of the seawater supply tube 220, the seawater can be made into fine particles and then sprayed. In addition, a side of the freshwater supply tube 226 may branch off to be connected to the pretreatment unit 260 and may spray fresh water into the pretreatment unit 260. Here, since a nozzle unit 262 is coupled to an end of the fresh water supply tube 226, fresh water can be made into fine particles and then sprayed. That is, the pretreatment unit 260 can selectively receive seawater, fresh water, and a mixture of seawater and fresh water.

When seawater, fresh water or a mixture of seawater and fresh water is sprayed into the pretreatment unit 260, fine dust in exhaust gas sinks as it absorbs water molecules. Accordingly, the exhaust gas supplied to the oxidation unit 250 via the pretreatment unit 260 may have reduced fine dust concentration. Since the exhaust gas with the reduced fine dust concentration is supplied to the oxidation unit 250, it is possible to prevent the fine dust from being adsorbed on an electrode (not illustrated) which is located inside the oxidation unit 250 and induces a pulsed corona discharge, thereby improving the oxidation efficiency of the exhaust gas. In addition, it is possible to prevent the fine dust from blocking the path of ultraviolet rays irradiated by the oxidation unit 250, thereby improving the oxidation efficiency.

The nozzle unit 262 is not necessarily coupled to each of the respective ends of the seawater supply tube 220 and the fresh water supply tube 226 and can be modified into various structures capable of spraying seawater or fresh water in the form of fine particles. For example, a water vapor generation unit (not illustrated) for generating water vapor may be coupled between the pretreatment unit 260 and the seawater supply tube 220 or between the pretreatment unit 260 and the fresh water supply tube 226. Here, the term "water vapor" may refer not only to a complete gas state of water but also to a state in which water in a liquid state is atomized to form small particles. The water vapor generated by the water vapor generation unit may be sprayed into the pretreatment unit 260 at a high pressure by a pumping unit (not illustrated).

A collecting tube 261 may be connected to a side of the pretreatment unit 260. The collecting tube 261 is a tube for supplying seawater or fresh water that has passed through the pretreatment unit 260 to the cleaning water supply tube 230 and may be selectively opened as needed. The collecting tube 261 may also supply the seawater or the fresh water that has passed through the pretreatment unit 260 to a circulation tube 291 which will be described later. That is, the collecting tube 261 may branch off to be connected to the cleaning water supply tube 230 or the circulation tube 291.

Sulfuric acid ($H_2SO_4$) and nitric acid ($HNO_3$) generated in the scrubber 240 may be neutralized by a neutralizing agent supplied from the neutralizing agent supply unit 300. For example, the neutralizing agent may be an alkaline solution, that is, sodium hydroxide (NaOH) or sodium hypochlorite (NaOCl) and may be obtained by electrolysis of seawater. Therefore, the neutralizing agent supply unit 300 may simply include a neutralizing agent tank that stores the neutralizing agent or may include an electrolysis device to produce the neutralizing agent by itself. When the neutralizing agent supply unit 300 includes the electrolysis device to produce the neutralizing agent by itself, a side of the neutralizing agent supply unit 300 may be connected to a seawater inlet tube 221 branching from the seawater supply tube 220 so as to receive seawater. At least one pump P2 may be installed on the seawater inlet tube 221 to smoothly supply seawater to the neutralizing agent supply unit 300.

The neutralizing agent supply unit 300 may supply the neutralizing agent to the scrubber 240, the seawater supply tube 220, or the collecting tube 261. In other words, the neutralizing agent supply unit 300 may supply the neutralizing agent to the scrubber 240 through a first injection tube 310, supply the neutralizing agent to the seawater supply tube 220 through a second injection tube 320, or supply the neutralizing agent to the collecting tube 261 through a third injection tube 330.

When the neutralizing agent supply unit 300 supplies the neutralizing agent to the scrubber 240, the cleaning water may be controlled to contact the exhaust gas first and then the neutralizing agent. That is, the exhaust gas and the cleaning water may first be brought into contact with each other so that microorganisms in the cleaning water can be killed by sulfuric acid and nitric acid. Then, the neutralizing agent may be mixed with the cleaning water to neutralize the cleaning water to an appropriate pH. Through this process, it is possible to remove contaminants from the exhaust gas in the scrubber 240, kill the microorganisms in the cleaning water, and neutralize the cleaning water at once.

As described above, seawater or fresh water that has passed through the pretreatment unit 260 flows inside the collecting tube 261. Since the seawater or the fresh water that has passed through the pretreatment unit 260 is acidic due to fine dust and contaminants contained therein, the neutralizing agent supply unit 300 may appropriately adjust the pH of the seawater or the fresh water by supplying the neutralizing agent.

The cleaning water discharge tube 241 is a tube for discharging cleaning water from the scrubber 240 and may be connected back to the seawater supply tube 220 by a filter unit 270. That is, the cleaning water discharge tube 241 may separate solid-phase particles from the cleaning water using the filter unit 270 and then discharge the cleaning water to the outside. The cleaning water discharge tube 241 is not necessarily connected to the seawater supply tube 220 and can also be independently connected to the outside of a ship.

The circulation tube 291 may be connected to the cleaning water discharge tube 241. The circulation tube 291 is a tube for recirculating the cleaning water discharged through the cleaning water discharge tube 241 to the cleaning water supply tube 230. When there is no need to discharge the cleaning water to the outside, the cleaning water may be circulated to the scrubber 40 and reused. A recirculation tank 290 may be installed between the cleaning water discharge tube 241 and the circulation tube 291. The recirculation tank 290 may store some of the cleaning water discharged from the scrubber 240 and may serve as a kind of buffer tank that allows a certain amount of cleaning water to be circulated through the circulation tube 291. The recirculation tank 290 may include any one of a centrifuge, a gravity separator and a filter to remove solid-phase particles from the cleaning water and to recirculate the cleaning water through the circulation tube 291.

Since the cleaning water supply tube 230 is connected to the seawater supply tube 220, the fresh water supply tube 226, the circulation tube 291 and the collecting tube 261, it can appropriately mix seawater, fresh water and circulating water in view of the concentration of the exhaust gas, the treatment capacity of the scrubber 240, the concentration and degree of contamination of the cleaning water, etc. and supply the mixture to the scrubber 240.

The filter unit 270 is installed behind the scrubber 240 to separate solid-phase particles from the cleaning water discharged from the scrubber 240. Like the recirculation tank 290, the filter unit 270 may separate solid-phase particles from the cleaning water using at least one of a centrifuge, a gravity separator and a filter and discharge the solid-phase particles to a sludge tank 280. The filter unit 270 may be connected to the seawater supply tube 220 between the pump P1 and the first control valve 225. That is, the seawater supplied from the seawater supply tube 220 may pass through the filter unit 270 and then may be supplied to the scrubber 240 through the cleaning water supply tube 230, and the cleaning water that has passed through the scrubber 240 may pass through the filter unit 270 again. That is, both the seawater introduced from the outside and the cleaning water that has passed through the scrubber 240 can be filtered by one filter unit 270. In addition, one or two filter units 270 can be used commonly or independently to remove materials having larges particles from the cleaning water that has passed through the cleaning water discharge tube 241 or the seawater that has passed through the seawater supply tube 220.

A neutralizing agent or a sterilizing agent may be sprayed to the cleaning water or the seawater, which has passed through the filter unit 270, through the second injection tube 320. The mixing tube 222 to which a mixture of the seawater and the cleaning water is discharged may be installed between the filter unit 270 and the seawater discharge tube 223, and the second injection tube 320 may be connected to the seawater supply tube 220 or the mixing tube 222. A sensor unit 24 may be installed on the seawater discharge tube 223 to identify, in real time, at least one of total residual oxidant, pH value, and microbial concentration of the cleaning water and the seawater to be discharged. The sensor unit 224 may be, for example, a total residual oxidant sensor, and the neutralizing agent supply unit 300 may adjust the supply of the oxidizing agent, the neutralizing agent and the sterilizing agent according to the result value of the sensor unit 224.

The cleaning water and the seawater discharged through the mixing tube 222 are discharged to the outside through the seawater discharge tube 223.

Figure 8:
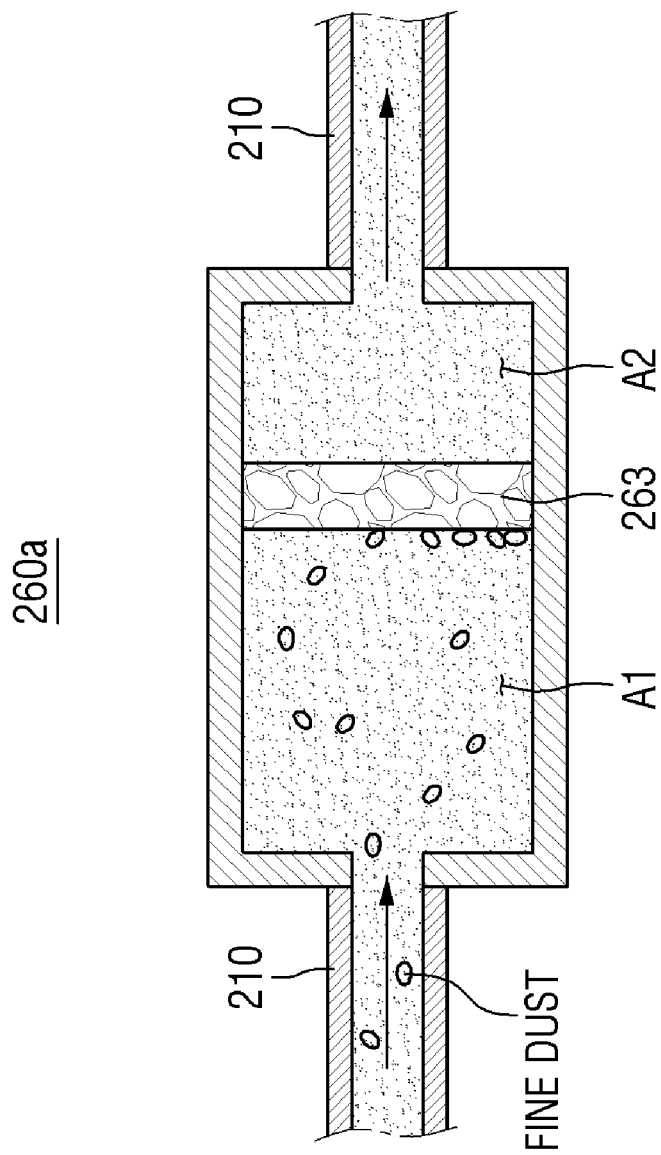
FIG. 8 is a cross-sectional view of another example of the pretreatment unit of FIG. 6.

FIG. 8 is a cross-sectional view of another example of the pretreatment unit of FIG. 6.

Referring to FIG. 8, a pretreatment unit 260a reduces the concentration of fine dust by using a separation membrane 263 having a low transmittance of fine dust. The pretreatment unit 260a according to the current embodiment of the inventive concept is substantially the same as that of the above-described embodiment, except that the fine dust concentration is reduced by, using the separation membrane 263 having a log transmittance of fine dust. Therefore, this difference will be mainly described, and the description of the other elements will be replaced by the above description unless otherwise stated.

The pretreatment unit 260a uses at least one separation membrane 263 to reduce the concentration of fine dust in exhaust gas to be introduced into the oxidation unit 250. The separation membrane 263 is a membrane which has a low transmittance of fine dust and thus blocks the transmission of fine dust. The separation membrane 263 used herein not limited to a membrane that can completely block the transmission of fine dust, and any separation membrane capable of controlling the concentration of fine dust can be used.

The separation membrane 263 may be installed inside the pretreatment unit 260a as illustrated in the drawing or may be installed inside the exhaust gas tube 210. In addition, the separation membrane 263 may be disposed in multiple stages along the moving direction of the exhaust gas to reduce the concentration of fine dust stage by stage.

The separation membrane 263 may laterally divide the pretreatment unit 260a into a first area A1 and a second area A2. The first area A1 and the second area A2 are formed on both sides of the separation membrane 263. The first area A1 may be connected to the combustion engine, and the second area A2 may be connected to the oxidation unit 250. Here, the second area A2 may be set to a lower pressure than the first area A1. Thus, the exhaust gas introduced through the exhaust gas tube 210 may flow from the first area A1 to the second area A2 via the separation membrane 263. Since the separation membrane 263 has a low transmittance of fine dust as described above, it can block the transmission of fine dust contained in the exhaust gas introduced through the exhaust gas tube 210. That is, the fine dust concentration of the exhaust gas present in the second area A2 can be kept lower than the fine dust concentration of the exhaust gas present in the first area A1.

Figure 9:
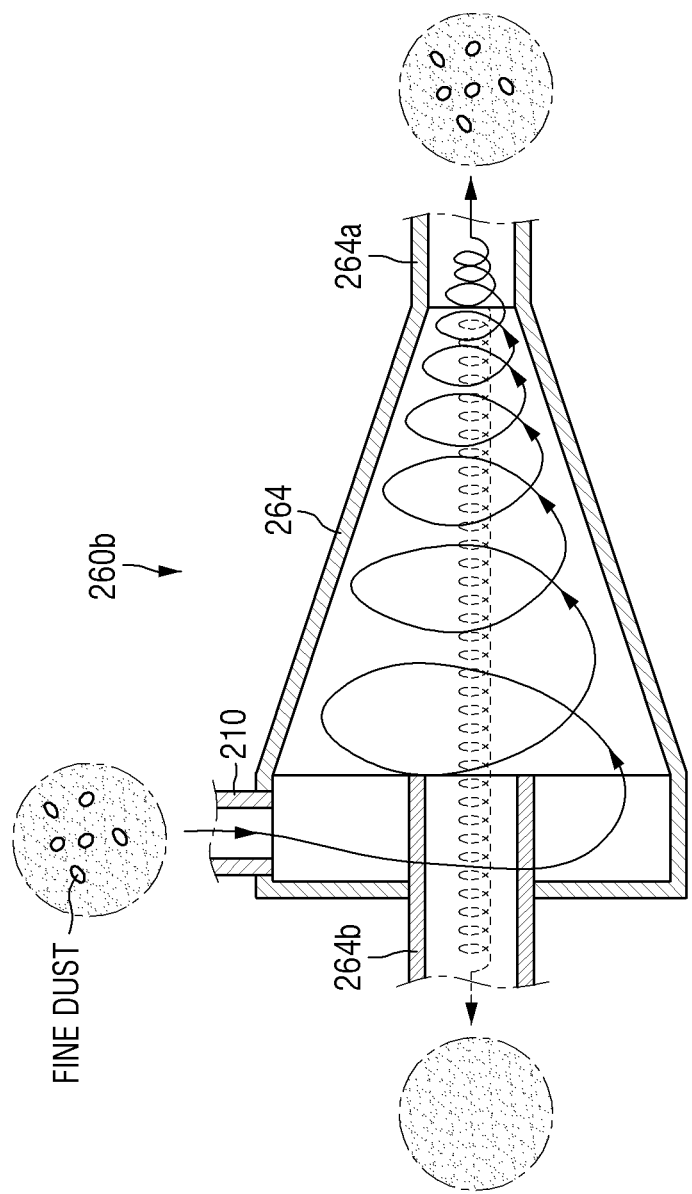
FIG. 9 is a cross-sectional view of another example of the pretreatment unit of FIG. 6.

FIG. 9 is a cross-sectional view of another example of the pretreatment unit of FIG. 6.

Referring to FIG. 9, a pretreatment unit 260b reduces concentration of fine dust by using a cyclone centrifuge 264. The pretreatment unit 260b according to the current embodiment of the inventive concept is substantially the same as those of the above-described embodiments, except that the fine dust concentration is reduced by using the cyclone centrifuge 264. Therefore, this difference will be mainly described, and the description of the other elements will be replaced by the above description unless otherwise stated.

The pretreatment unit 260b receives exhaust gas through the exhaust gas tube 210 and separates fine dust from the exhaust gas. Here, the centrifuge 264 can be used. The centrifuge 264 is formed as a cyclone solid separator as illustrated in the drawing. That is, when the exhaust gas containing the fine dust is supplied from the exhaust gas tube 210 into the centrifuge 264 in a tangential direction, it is divided into exhaust gas without the fine dust and the fine dust by the difference in density. The fine dust gathers on a conical wall while being rotated by a centrifugal force and is discharged through a conical portion 264a. The exhaust gas without the fine dust gathers in a central portion of the centrifuge 264 to rise while forming a swirling vortex and is discharged through a cylindrical portion 264b. The fine dust and the fine dust-containing exhaust gas discharged through the conical portion 264a, are supplied to a particle eliminator, and the exhaust gas without the fine dust discharged through the cylindrical portion 264b is supplied to the oxidation unit 250 through the exhaust gas tube 210.

The operation of the contaminant reducing device 200 will now be described in more detail with reference to FIGS. 10 and 11.

Figure 10:
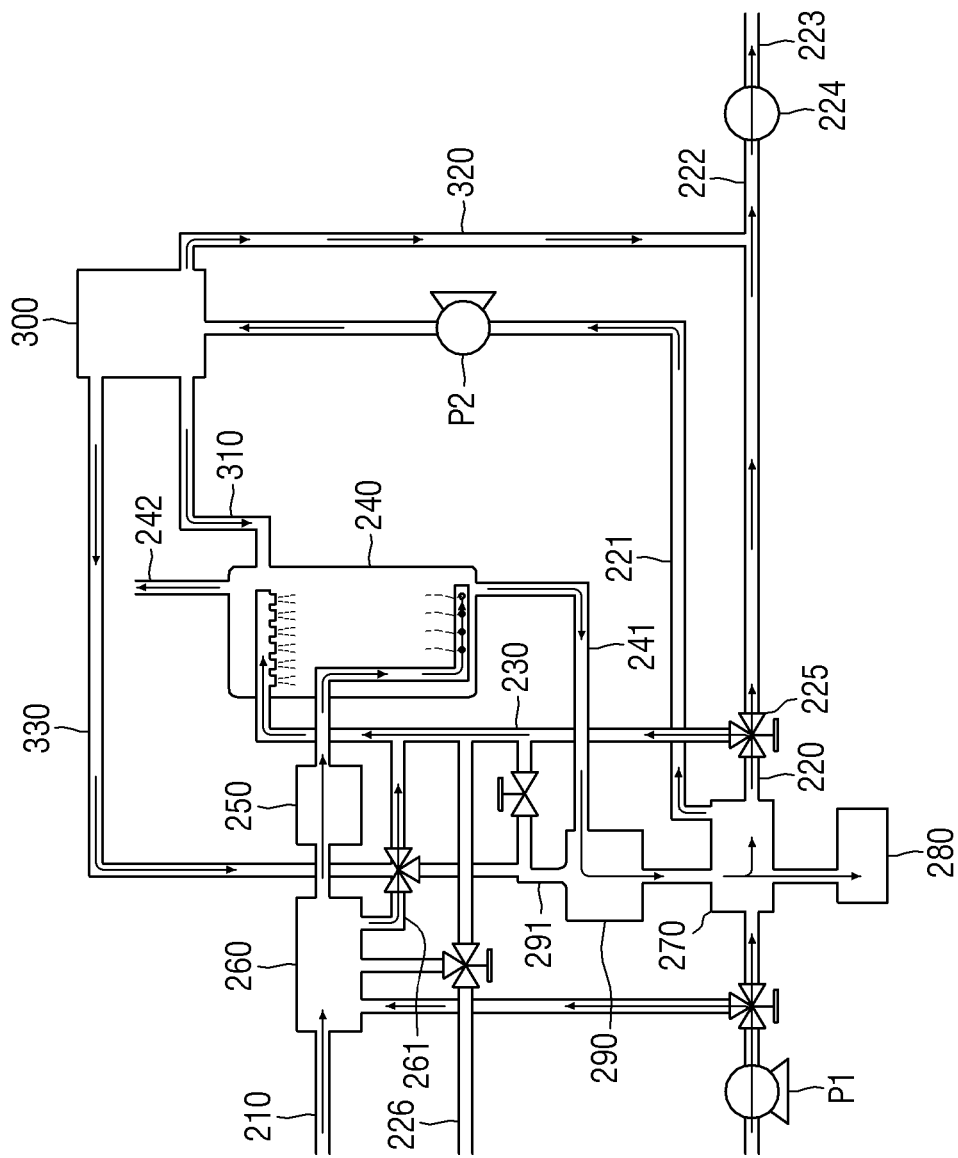
FIGS. 10 and 11 illustrate the operation of the contaminant reducing device according to the second embodiment of the inventive concept.
Figure 11:
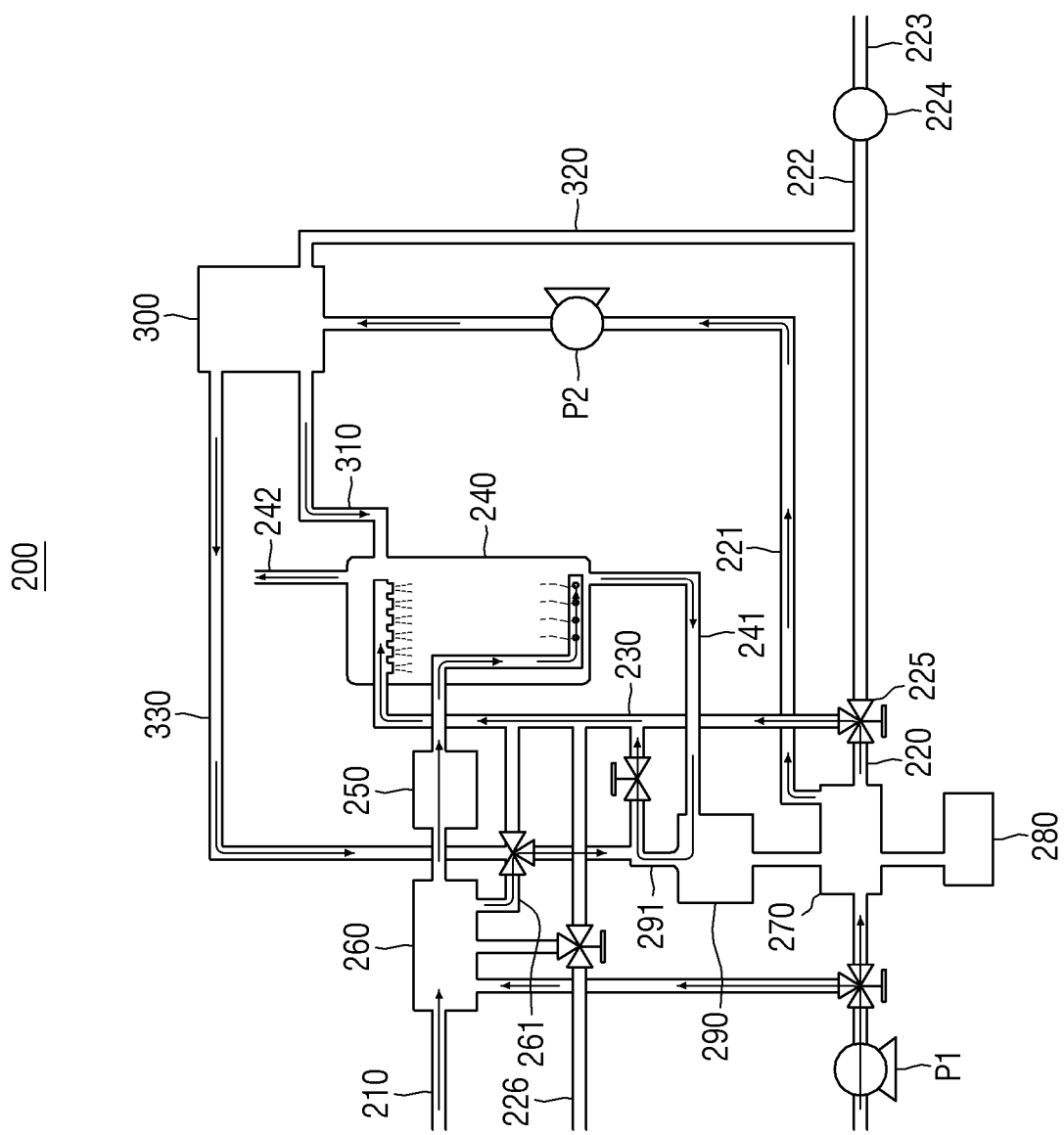

FIG. 10 illustrates an open loop mode in which seawater supplied to the seawater supply tube is directly discharged to the outside after passing through the scrubber, and FIG. 11 illustrates a closed loop mode in which seawater supplied to the seawater supply tube is recirculated through the circulation tube after passing through the scrubber.

Referring to FIG. 10, some of the seawater introduced through the seawater supply tube 220 may be supplied to the scrubber 240 through the cleaning water supply tube 230, and some of the seawater may be supplied to the neutralizing agent supply unit 300 through the seawater inlet tube 221. Cleaning water may be sprayed from the upper part of the scrubber 240 and fill the lower part of the scrubber 240 to a certain level. At this time, exhaust gas supplied through the exhaust gas tube 210 may sequentially pass through the pretreatment unit 260 and the oxidation unit 250 and then be sprayed from the lower part of the scrubber 240. The pretreatment unit 260 may receive the seawater from the seawater supply tube 220 and spray the seawater to fine dust. The oxidation unit 250 may oxidize nitrogen monoxide contained in the exhaust gas to nitrogen dioxide through pulsed corona discharge or irradiation of ultraviolet rays.

The neutralizing agent supply unit 300 may generate a neutralizing agent by electrolyzing the seawater and may spray the neutralizing agent into the seawater supply tube 220 or the scrubber 240 in view of the pH value of the cleaning water. In addition, the neutralizing agent supply unit 300 may adjust the pH of the seawater flowing through the collecting tube 261 after passing through the pretreatment unit 260 by spraying the neutralizing agent to the seawater The pH-adjusted seawater inside the collecting tube 261 may be supplied to the scrubber 240 through the cleaning water supply tube 230.

Since the exhaust gas can be sprayed within the cleaning water filling the lower part of the scrubber 240, contaminants such as nitrogen oxides, sulfur oxides and dust can be removed. In addition, the contaminants can be removed again by the cleaning water sprayed from the upper part of the scrubber 240. Through this process, the contaminants contained in the exhaust gas are removed, and the exhaust gas from which the contaminants have been removed is discharged to the outside through the discharge tube 242.

The cleaning water that has passed through the scrubber 240 contains contaminants such as nitrogen oxides, sulfur oxides and dust and moves to the filter unit 270 through the cleaning water discharge tube 241. The filter unit 270 separates contaminants such as solid-phase particles from the cleaning water and stores the separated contaminants in the sludge tank 280. The cleaning water from which the contaminants have been removed is discharged to the outside through the seawater discharge tube 223. Here, if the total residual oxidant and pH value (measured by the sensor unit 224) of the cleaning water passing through the seawater discharge tube 223 are outside a reference range, they are adjusted to be within the reference range by injecting (not illustrated) sodium thiosulfate into the mixing tube 222 or injecting the neutralizing agent produced in the neutralizing agent supply unit 300 into the scrubber 240 through the first injection tube 310. Then, the cleaning water is discharged to the outside.

Referring to FIG. 11, some of the seawater introduced through the seawater supply tube 220 is supplied to the scrubber 240 and used as cleaning water, and some of the seawater is supplied to the neutralizing agent supply unit 300 and used to generate a neutralizing agent. Exhaust gas supplied through the exhaust gas tube 210 sequentially passes through the pretreatment unit 260 and the oxidation unit 250 and then is sprayed into the scrubber 240. The pretreatment unit 260 reduces the concentration of fine dust in the exhaust gas by spraying the seawater supplied from the seawater supply tube 220 to the fine dust.

The cleaning water discharged to the cleaning water discharge tube 241 via the scrubber 240 is temporarily stored in the recirculation tank 290 and then circulated back to the cleaning water supply tube 230 through the circulation tube 291.

The neutralizing agent supply unit 300 sprays the neutralizing agent into the scrubber 240 and the collecting tube 261 in view of the pH value of the cleaning water, and the pH-adjusted seawater inside the collecting tube 261 may be supplied to the circulation tube 291.

The seawater introduced through the seawater supply tube 220 is circulated sequentially through the cleaning water supply tube 230, the scrubber 240, the cleaning water discharge tube 241, the recirculation tank 290 and the circulation tube 291. The process of FIG. 10 and the process of FIG. 11 may be performed together in view of the degree of contamination, pH value, etc. of the seawater. The process of FIG. 11 may be used when the seawater cannot be discharged to the outside, for example, when the ship is passing through an area where the discharge of the seawater is restricted.

Hereinafter, a contaminant reducing device according to a third embodiment of the inventive concept will be described in detail with reference to FIGS. 12 through 14.

The contaminant reducing device according to the third embodiment of the inventive concept can prevent the reduction of oxidized sulfur oxides and nitrogen oxides by injecting a liquid catalyst into the oxidized sulfur oxides and nitrogen oxides before a gas-liquid contact. Therefore, the reduction effect of the sulfur oxides and the nitrogen oxides can be improved. In addition, since the oxidized exhaust gas is double purified as it passes through a wet scrubber, contaminants in the exhaust gas can be significantly reduced.

Figure 12:
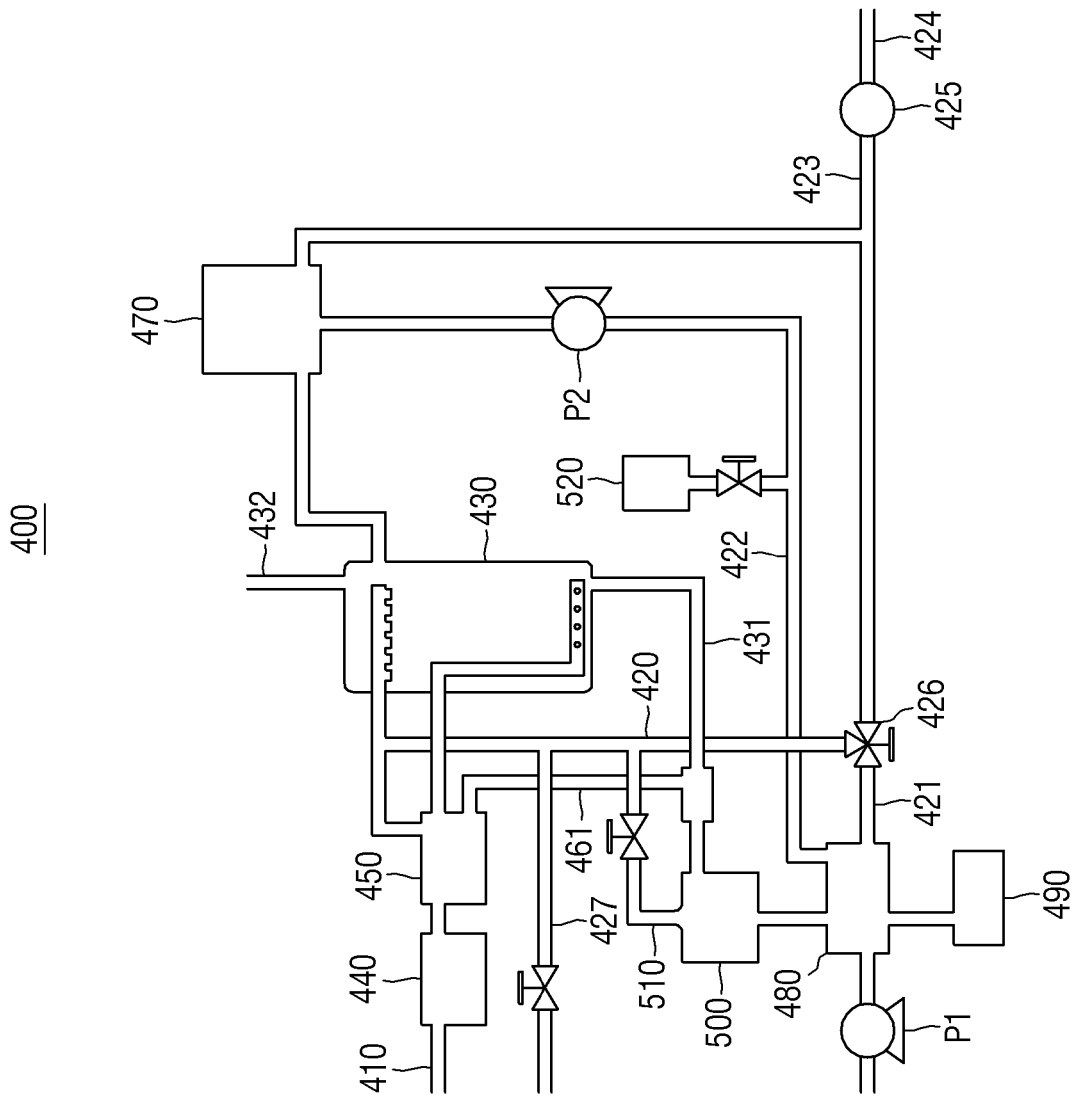
FIG. 12 is a schematic view of a contaminant reducing device according to a third embodiment of the inventive concept.

FIG. 12 is a schematic view of a contaminant reducing device according to a third embodiment of the inventive concept.

The contaminant reducing device 400 according to the inventive concept includes an exhaust gas tube 410, a cleaning water supply tube 420, a scrubber 430, an oxidation unit 440, a liquid catalyst injection unit 450, and a cleaning water discharge tube 431.

The exhaust gas tube 410 is a tube through which exhaust gas moves from a combustion engine (not illustrated) and is connected to the scrubber 430 which will be described later. The exhaust gas tube 410 may be directly connected to an exhaust tube of the combustion engine and serve as a passage through which hot exhaust gas moves or waste gas remaining after most of the exhaust heat is recycled by various heat exchangers moves. The generated exhaust gas contains a large amount of nitrogen oxides, sulfur oxides and dust and is supplied to the scrubber 430 through the exhaust gas tube 410 connected to a side of the combustion engine.

The cleaning water supply tube 420 is a tube for supplying the scrubber 430 with cleaning water which is at least one of seawater, fresh water, and a mixture of seawater and fresh water. An end of the cleaning water supply tube 420 may be connected to a seawater supply tube 421 or a fresh water supply tube 427, and the other end of the cleaning water supply tube 420 may be connected to the scrubber 430.

The seawater supply tube 421 is a tube through which seawater is supplied from the outside, and at least one pump P1 for pressurizing seawater is installed on the seawater supply tube 421 to smoothly supply seawater to the scrubber 430. However, the inventive concept is not limited to this case.

The cleaning water supply tube 420 may branch from a side of the seawater supply tube 421 and may be connected to the scrubber 430. A control valve 426 may be installed at a connection portion between the seawater supply tube 421 and the cleaning water supply tube 420. The control valve 426 may be formed as a three-way valve to control the amount of seawater supplied to the cleaning water supply tube 420 or appropriately adjust a ratio of seawater supplied to the cleaning water supply tube 420 to seawater supplied to the seawater supply tube 421.

The seawater introduced from the outside through the seawater supply tube 421 is supplied to the scrubber 430 via the cleaning water supply tube 420. The scrubber 430 is a device for spraying cleaning water supplied through the cleaning water supply tube 420 to exhaust gas supplied through the exhaust gas tube 410 in order to bring the exhaust gas and the cleaning water into contact with each other. The scrubber 430 may be a typical wet scrubber. Here, an end of the cleaning water supply tube which is disposed inside the scrubber 430 may be located in an upper part of the scrubber 430 and may branch into a plurality of parts to spray the cleaning water in the form of fine particles.

The cleaning water, which has absorbed nitrogen oxides, sulfur oxides and dust through the contact with the contaminant-containing exhaust gas in the scrubber 430, is discharged out of the scrubber 430 through the cleaning water discharge tube 431.

The exhaust gas supplied through the exhaust gas tube 410 may first be purified by the oxidation unit 440 and then purified again by the scrubber 430.

The oxidation unit 440 is a device for oxidizing exhaust gas by performing a pulsed corona discharge, irradiating ultraviolet rays or spraying an oxidizing agent and may be connected to the exhaust gas tube 410. In other words, nitrogen monoxide contained in the exhaust gas flowing through the exhaust gas tube 410 can be oxidized to nitrogen dioxide by the oxidation unit 440. The nitrogen dioxide is easily dissolved in water as compared with the nitrogen monoxide. Therefore, the nitrogen dioxide can be easily dissolved and removed in the cleaning water in the scrubber 430.

In a case where the oxidation unit 440 oxidizes the exhaust gas by performing a pulsed corona discharge, when a corona discharge occurs due to a pulsed high voltage, the exhaust gas becomes a plasma state and generates ozone and oxidative radicals such as $O_2$ and OH to oxidize nitrogen oxides or sulfur oxides. In addition, in a case where the oxidation unit 440 oxidizes the exhaust gas by spraying an oxidizing agent, a liquid oxidizing agent may be atomized, dropletized or vaporized using a nozzle, an ultrasonic vibrator, a spray, a heating plate, or the like.

The exhaust gas purified by the oxidation unit 440 may pass through the liquid catalyst injection unit 450 before being supplied to the scrubber 430.

The liquid catalyst injection unit 450 is a device for maintaining exhaust gas in an oxidized state and may be connected to the exhaust gas tube 410 located behind the oxidation unit 440. The exhaust gas that has been artificially oxidized by the oxidation unit 440 can be easily reduced to its original state. If the exhaust gas is reduced, it is not easily dissolved and removed in the cleaning water inside the scrubber 430. Therefore, the exhaust gas should be controlled to be introduced into the scrubber 430 in the oxidized state. The liquid catalyst injection unit 450 maintains the exhaust gas in the oxidized state by injecting a liquid catalyst into the oxidized exhaust gas. The liquid catalyst may be organic sulfoxides obtained by oxidizing organic sulfides contained in oil such as petroleum or diesel, and a weight ratio of water and sulfoxide may be 30 to 70: 70 to 30. Since the liquid catalyst, which is organic sulfoxides, is injected into the oxidized exhaust gas, the exhaust gas can be supplied to the scrubber 430 in the oxidized state without being reduced. However, the liquid catalyst injection unit 450 is not necessarily connected to the exhaust gas tube 410 behind the oxidation unit 440 or to the cleaning water supply tube 420, and the position of the liquid catalyst injection unit 450 can vary. For example, the liquid catalyst injection unit 450 may be formed inside the oxidation unit 440 to be integrated with or separated from the oxidation unit 440 or may be formed inside the scrubber 430 to be integrated with or separated from the scrubber 430.

Sulfuric acid and nitric acid generated the scrubber 430 may be neutralized by a neutralizing agent supplied from a neutralizing agent supply unit 470. For example, the neutralizing agent may be an alkaline solution, that is, sodium hydroxide (NaOH) or sodium hypochlorite (NaOCl) and may be obtained by electrolysis of seawater. Therefore, the neutralizing agent supply unit 470 may simply be formed as a neutralizing agent tank that stores the neutralizing agent or may include an electrolysis device to produce the neutralizing agent by itself. When the neutralizing agent supply unit 470 includes the electrolysis device to produce the neutralizing agent by itself, a side of the neutralizing agent supply unit 470 may be connected to a seawater inlet tube 422 branching from the seawater supply tube 421 so as to receive seawater. At least one pump P2 may be installed on the seawater inlet tube 422 to smoothly supply seawater to the neutralizing agent supply unit 470.

The neutralizing agent supply unit 470 may supply the neutralizing agent to the scrubber 430 or the seawater supply tube 421. When the neutralizing agent supply unit 470 supplies the neutralizing agent to the scrubber 430, the cleaning water may be controlled to contact the exhaust gas first and then the neutralizing agent.

An electrolyte tank 520 for supplying an electrolyte to seawater may be provided on the seawater supply tube 421 or the seawater inlet tube 422 branching from the seawater supply tube 421. Here the electrolyte moray be sodium chloride (NaCl).

The cleaning water discharge tube 431 is a tube for discharging cleaning water from the scrubber 430 and may be connected to the seawater supply tube 421 by a filter unit 480.

A separation unit 460 may be provided on and connected to cleaning water discharge tube 431. The separation unit 460 is a device for separating a liquid catalyst from cleaning water and may separate the liquid catalyst from the cleaning water using the difference in specific gravity between the liquid catalyst and the cleaning water. That is, the separation unit 460 separates the liquid catalyst from the cleaning water using a gravity separation method. The liquid catalyst has a specific gravity of about 0.85 which is smaller than that of the cleaning water. Therefore, the cleaning water having a relatively large specific gravity is disposed in a lower part of the separation unit 460, and the liquid catalyst having a small specific gravity is disposed in an upper part of the separation unit 460, so that the cleaning water and the liquid catalyst can be completely separated from each other. However, the separation unit 460 can separate the liquid catalyst from the cleaning water not just using the gravity separation method but in various ways. Since the separation unit 460 separates the liquid catalyst from the cleaning water, it is possible to prevent the liquid catalyst from being discharged out of the ship together with the cleaning water when the contaminant reducing device 400 operates in an open loop mode. The separated liquid catalyst may be circulated to the liquid catalyst injection unit 450.

A circulation line 461 is a tube for recirculating the liquid catalyst separated by the separation unit 460 to the liquid catalyst injection unit 450 and may connect the separation unit 460 and the liquid catalyst injection unit 450 to each other. The circulation line 461 may be opened when the cleaning water is discharged to the outside, that is, when the contaminant reducing device 400 operates in the open loop mode, so that the liquid catalyst can be circulated to the liquid catalyst injection unit 450.

A recirculation tube 510 may also be connected to the cleaning water discharge tube 431.

A recirculation tank 500 may be installed between the cleaning water discharge tube 431 and the recirculation tube 510. The recirculation tank 500 may include any one of a centrifuge, a gravity separator and a filter to remove solid-phase particles from the cleaning water and to recirculate the cleaning water through the circulation tube 510.

Since the cleaning water supply tube 420 is connected to the seawater supply tube 421, the fresh water supply tube 427 and the recirculation tube 510, it can appropriately mix seawater, fresh water and circulating water in view of the concentration of the exhaust gas, the treatment capacity of the scrubber 430, the concentration degree of contamination of the cleaning water, etc. and supply the mixture to the scrubber 430.

The filter unit 480 is installed behind the scrubber 430 to separate solid-phase particles from the cleaning water discharged from the scrubber 430. Like the recirculation tank 500, the filter unit 480 may separate solid-phase particles from the cleaning water using at least one of a centrifuge, a gravity separator and a filter and discharge the solid-phase particles to a sludge tank 490.

A neutralizing agent may be injected from the neutralizing agent supply unit 470 into the cleaning water or seawater that has passed through the filter unit 480. The neutralizing agent may be injected into a mixing tube 423 into which a mixture of the seawater and the cleaning water is discharged, and the mixing tube 423 may connect the filter unit 480 and a seawater discharge tube 424. A sensor unit 425 is installed on the seawater discharge tube 424.

The operation of the contaminant reducing device 400 will now be described in more detail with reference to FIGS. 13 and 14. FIGS. 13 and 14 illustrate the operation of the contaminant reducing device according to the third embodiment of the inventive concept.

The contaminant reducing device 400 according to the inventive concept can prevent the reduction of oxidized sulfur oxides and nitrogen oxides by injecting a liquid catalyst into the oxidized sulfur oxides and nitrogen oxides before a gas-liquid contact. Therefore, the reduction effect of the sulfur oxides and the nitrogen oxides can be improved. In addition, since the oxidized exhaust gas is double purified as it passes through a wet scrubber, contaminants in the exhaust gas can be significantly reduced.

Figure 13:
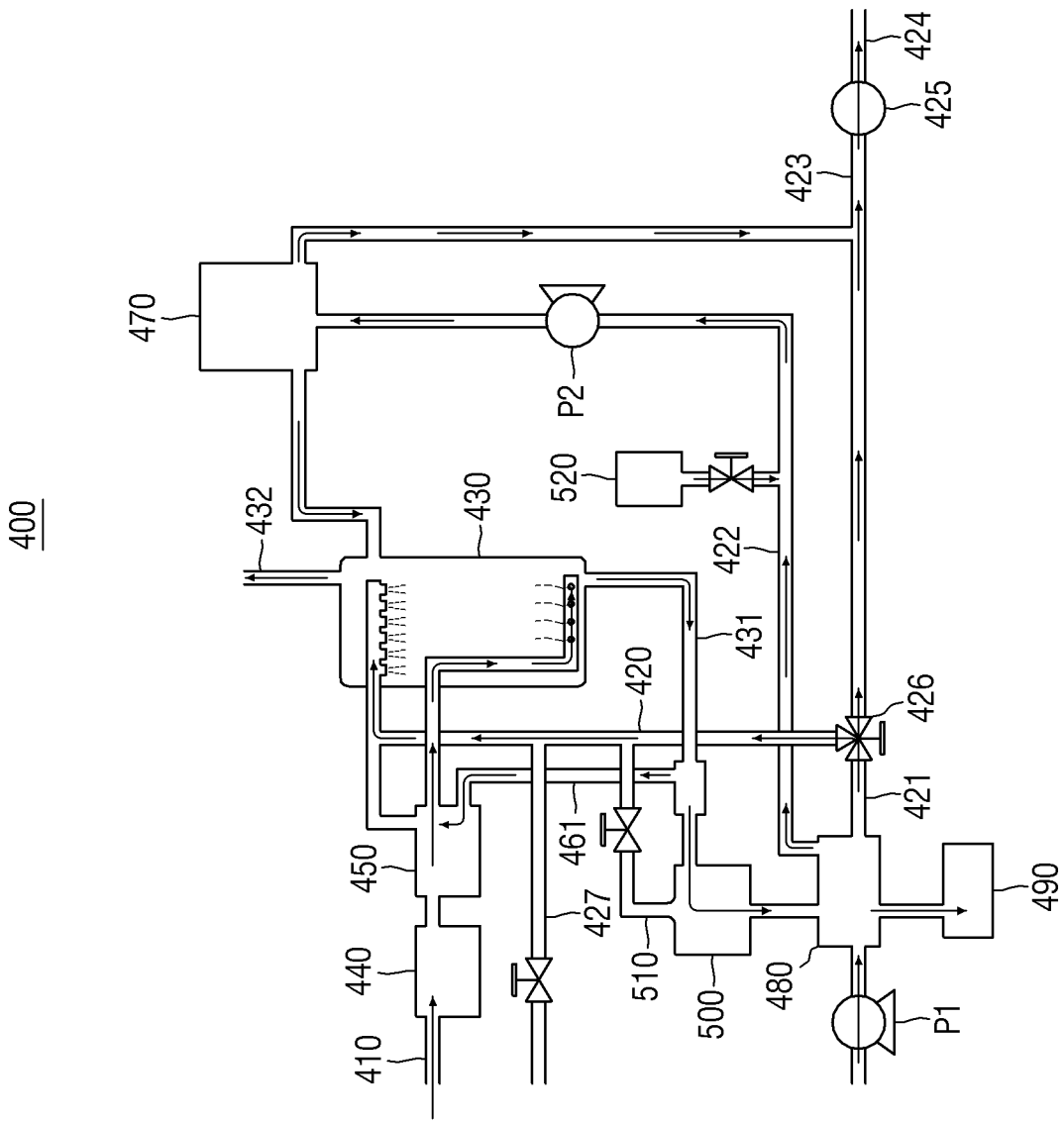
FIGS. 13 and 14 illustrate the operation of the contaminant reducing device according to the third embodiment of the inventive concept.
Figure 14:
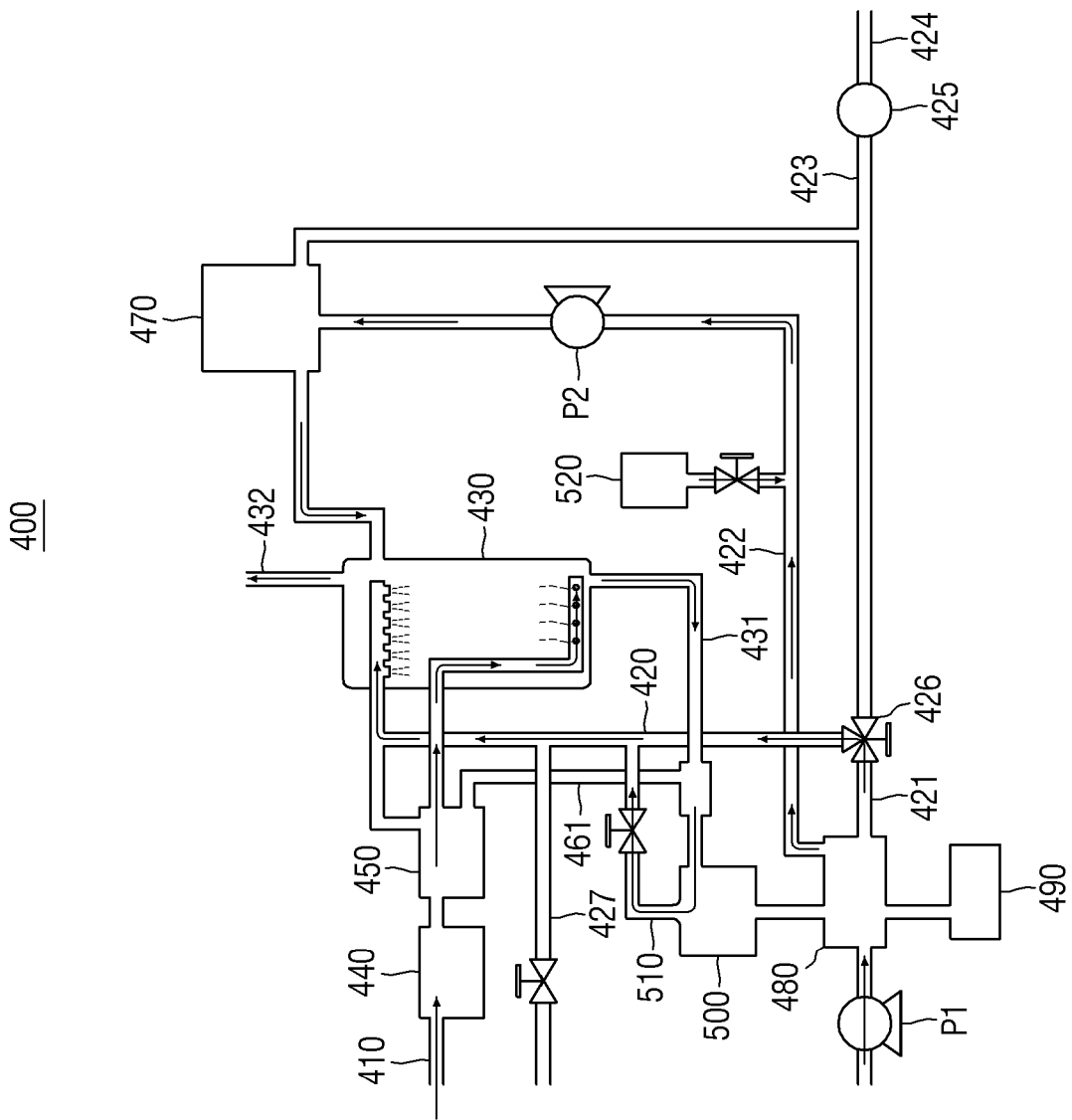

FIG. 13 illustrates an open loop mode in which seawater is discharged to the outside after passing through the scrubber, and FIG. 14 illustrates a closed loop mode in which seawater is recirculated through the recirculation tube after passing through the scrubber.

Referring to FIG. 13, some of the seawater introduced through the seawater supply tube 421 is supplied to the scrubber 430 through the cleaning water supply tube 420, and the rest of the seawater is supplied to the neutralizing agent supply unit 470 through the seawater inlet tube 422. Cleaning water may be sprayed downward from the upper part of the scrubber 430 and may gradually fill the lower part of the scrubber 430. At this time, exhaust gas supplied through the exhaust gas tube 410 may sequentially pass through the oxidation unit 440 and the liquid catalyst injection unit 450 and then be sprayed upward from the lower part of the scrubber 440 in the oxidized state. The oxidation unit 440 oxidizes nitrogen monoxide contained in the exhaust gas into nitrogen dioxide by discharging electricity, irradiating ultraviolet rays, or spraying an oxidizing agent. The liquid catalyst injection unit 450 maintains the exhaust gas in the oxidized state by injecting a liquid catalyst into the oxidized exhaust gas.

The neutralizing agent supply unit 470 may store or generate a neutralizing agent and spray the neutralizing agent to the seawater supply tube 421 or the scrubber 430 in view of the pH value of the cleaning water.

Since the exhaust gas is sprayed within the cleaning water filling the lower part of the scrubber 430, contaminants such as nitrogen oxides, sulfur oxides and dust can be removed. In addition, the contaminants can be removed again by the cleaning water sprayed from the upper part of the scrubber 430. Through this process, the contaminants contained in the exhaust gas are removed, and the exhaust gas from which the contaminants have been removed is discharged to the outside through a discharge tube 432.

The cleaning water that has passed through the scrubber 430 contains contaminants such as nitrogen oxides, sulfur oxides and dust and is discharged out of the scrubber 430 through the cleaning water discharge tube 431. Since the separation unit 460 is installed on the cleaning water discharge tube 431, the liquid catalyst is separated from the cleaning water and circulated to the liquid catalyst injection unit 450 through the circulation line 461, and only the cleaning water from which the liquid catalyst has been separated moves to the filter unit 480. The filter unit 480 separates contaminants such as solid-phase particles from the cleaning water and stores the separated contaminants in the sludge tank 490. The cleaning water from which the contaminants have been separated is discharged out of a ship through the seawater discharge tube 424. Here, if the total residual oxidant and pH value (measured by the sensor unit 425) of the cleaning water passing through the seawater discharge tube 424 are outside a reference range, they are adjusted. to be within the reference range by injecting the neutralizing agent from the neutralizing agent supply unit 470 into the scrubber 430 or the mixing tube 423. Then, the cleaning water is discharged to the outside.

When seawater containing a small amount of sodium chloride is introduced through the seawater supply tube 421, the electrolyte tank 520 may supply an electrolyte to the seawater flowing through the seawater inlet tube 422.

Referring to FIG. 14, some of the seawater introduced through the seawater supply tube 421 is supplied to the scrubber 430, and some of the seawater is supplied to the neutralizing agent supply unit 470. Cleaning water containing a liquid catalyst and supplied to the cleaning water discharge tube 431 via the scrubber 430 is temporarily stored in the recirculation tank 500 and then supplied back to the cleaning water supply tube 420 through the recirculation tube 510. That is, the remaining process of FIG. 14 is the same as that of FIG. 13 except that the cleaning water containing the liquid catalyst and discharged through the cleaning water discharge tube 431 is not discharged out of the ship but is recirculated to the cleaning water supply tube 420 through the recirculation tube 510.

The liquid catalyst that has been injected into oxidized exhaust gas by the liquid catalyst injection tube 450 is circulated sequentially through the exhaust gas tube 410, the scrubber 430, the cleaning water discharge tube 431, the separation unit 460 and the circulation line 461. The process of FIG. 13 and the process of FIG. 14 may be performed together in view of the degree of contamination of the liquid catalyst.

In addition, the seawater introduced through the seawater supply tube 421 is circulated sequentially through the cleaning water supply tube 420, the scrubber 430, the cleaning water discharge tube 431, the separation unit 460, the recirculation tank 500 and the recirculation tube 510. The process of FIG. 13 and the process of FIG. 14 may be performed together in view of the degree of contamination, pH value, etc. of the cleaning water.

The process of FIG. 14 may be used when the seawater cannot be discharged to the outside, for example, when the ship is passing through an area where the discharge of the seawater is restricted. The process of FIG. 13 and the process of FIG. 14 may be performed selectively or sequentially as needed.

Figure 15:
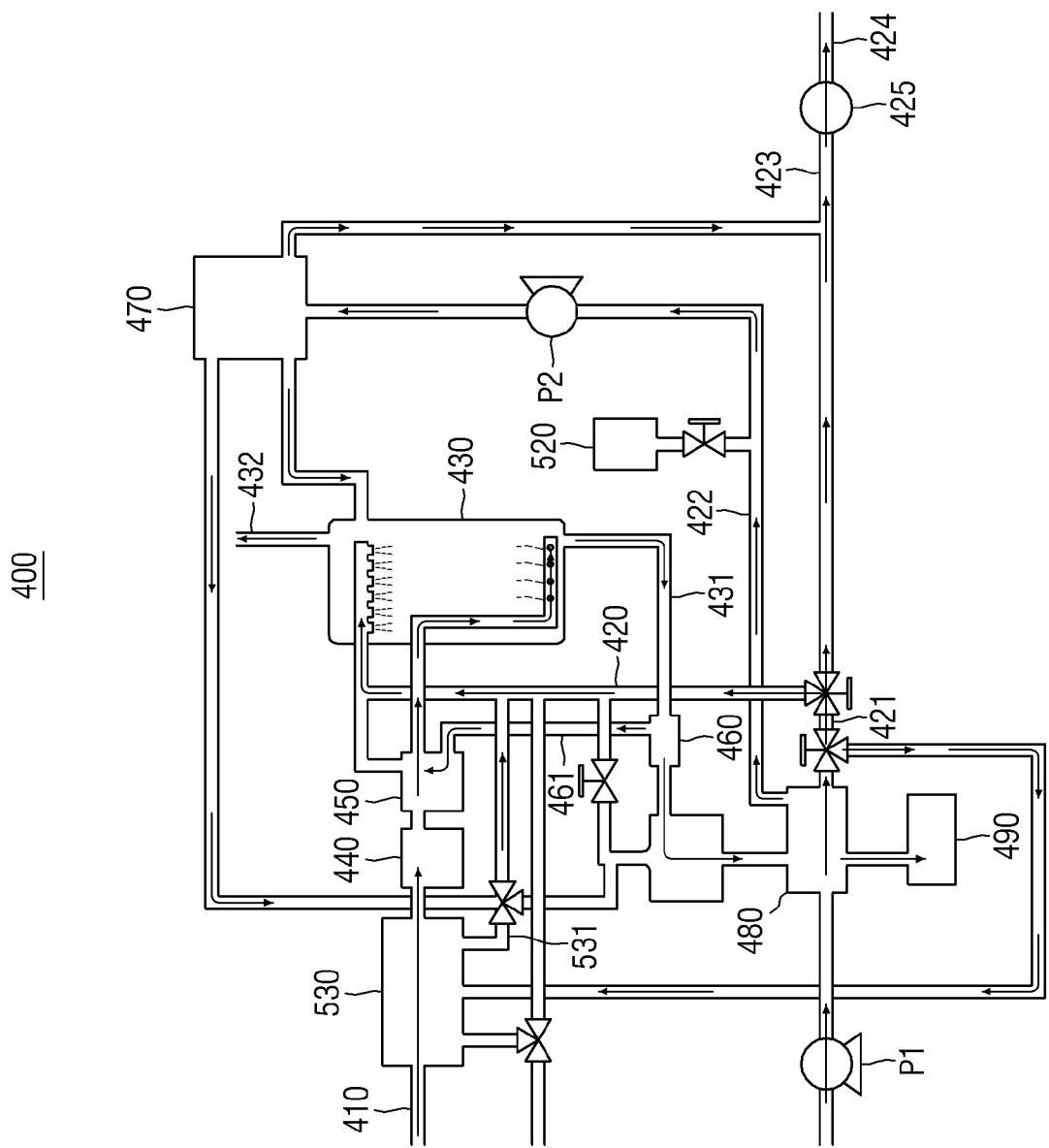
FIGS. 15 and 16 illustrate operation of a contaminant reducing device according to a fourth embodiment of the inventive concept.
Figure 16:
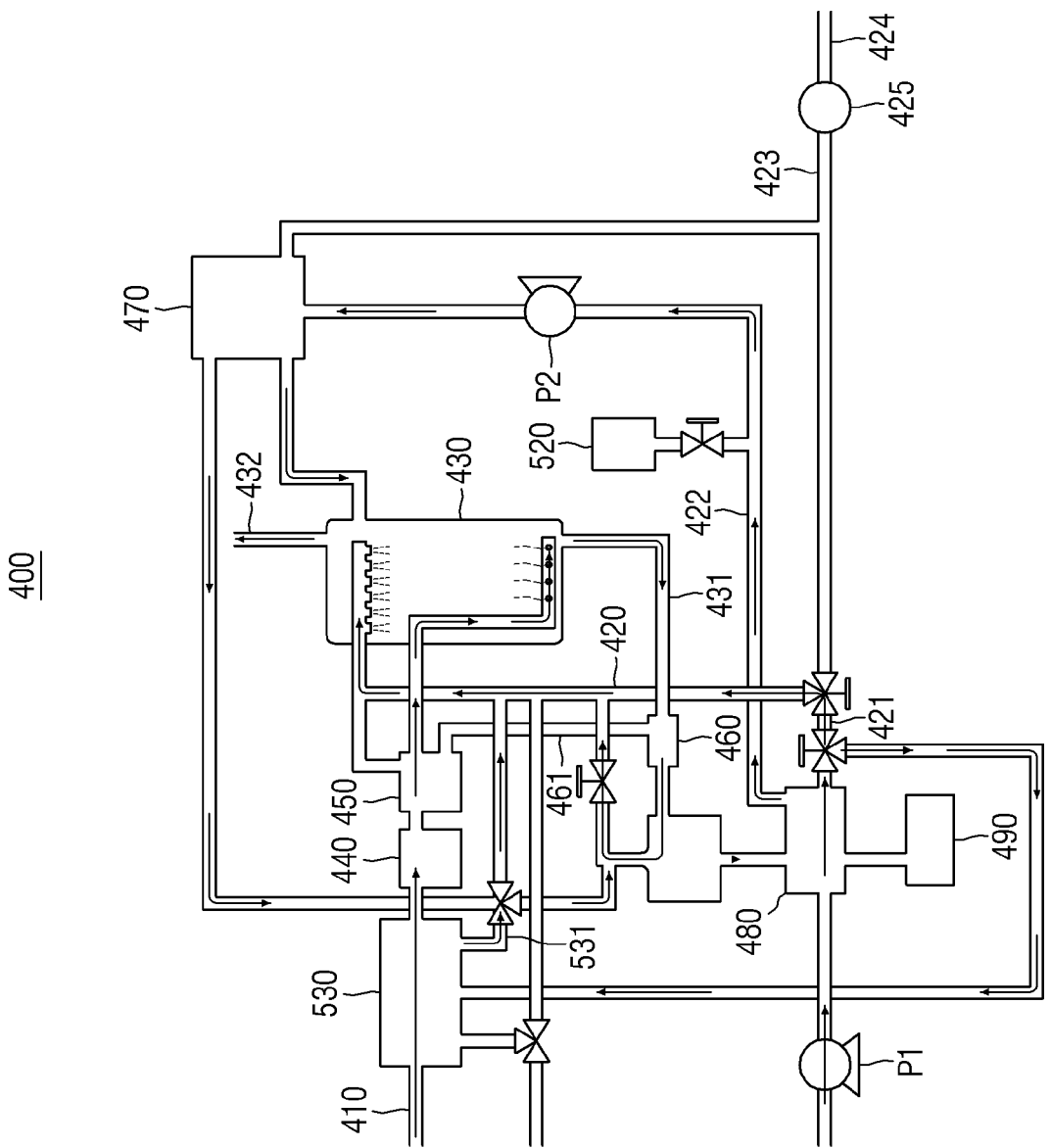

Hereinafter, a contaminant reducing device 400 according to a fourth embodiment of the inventive concept will be described in detail with reference to FIGS. 15 and 16. FIGS. 15 and 16 illustrate the operation of a contaminant reducing device according to a fourth embodiment of the inventive concept.

The contaminant reducing device 400 according to the fourth embodiment of the inventive concept further includes a pretreatment unit 530 for removing fine dust contained in exhaust gas. The contaminant reducing device 400 according to the fourth embodiment of the inventive concept is substantially the same as those of the above-described embodiments, except that it further includes the pretreatment unit 530 for removing fine dust contained in exhaust gas. Therefore, this difference will be mainly described, and the description of the other elements will be replaced by the above description unless otherwise stated.

The pretreatment unit 530 is a device for removing fine dust contained in exhaust gas and may be connected to an exhaust gas tube 410 located in front of an oxidation unit 440. The pretreatment unit 530 may reduce the concentration of fine dust in exhaust gas by spraying water molecules to the fine dust, by using a separation membrane having a low transmittance of fine dust, or by using a cyclone centrifuge.

A side of a seawater supply tube 421 may branch off to be connected to the pretreatment unit 530 and may spray seawater introduced from the outside into the pretreatment unit 530. Here, the seawater supply tube 421 may branch off behind a filter unit 480 to supply filtered seawater to the pretreatment unit 530. Since a nozzle unit (not illustrated) is formed at an end of the seawater supply tube 421, the seawater be made into fine particles and then sprayed. In addition, a side of a freshwater supply tube 427 may branch off to be connected to the pretreatment unit 530 and may spray fresh water into the pretreatment unit 530. Here, since a nozzle unit (not illustrated) is formed at an end of the fresh water supply tube 427, fresh water can be made into fine particles and then sprayed. That is, the pretreatment unit 530 can selectively receive seawater, fresh water, and a mixture of seawater and fresh water. However, the nozzle unit is not necessarily coupled to each of the respective ends of the seawater supply tube 421 and the fresh water supply tube 427 and can be modified into various structures capable of spraying seawater or fresh water in the form of fine particles. For example, a water vapor generation unit (not illustrated) for generating water vapor may be coupled between the pretreatment unit 530 and the seawater supply tube 421 or between the pretreatment unit 530 and the fresh water supply tube 427. Here, the term "water vapor" may refer not only to a complete gas state of water but also to a state in which water in a liquid state is atomized to form small particles. The water vapor generated by the water vapor generation unit may be sprayed into the pretreatment unit 530 at a high pressure by a pumping unit (not illustrated).

When seawater, fresh water or a mixture of seawater and fresh water is sprayed into the pretreatment unit 530, the fine dust the in exhaust gas sinks as it absorbs water molecules. Accordingly, the exhaust gas supplied to the oxidation unit 440 via the pretreatment unit 530 may have reduced fine dust concentration. Since the exhaust gas with the reduced fine dust concentration is supplied to the oxidation unit 440, it is possible to prevent the fine dust from being adsorbed on an electrode (not illustrated) which is located inside the oxidation unit 440 and induces a pulsed corona discharge, thereby improving the oxidation efficiency of the exhaust gas. In addition, it is possible to prevent the fine dust from blocking the path of ultraviolet rays irradiated by the oxidation unit 440, thereby improving the oxidation efficiency.

A collecting tube 531 may be connected to a side of the pretreatment unit 530. The collecting tube 531 is a tube for collecting seawater or fresh water that has passed through the pretreatment unit 530 and supplying the seawater or the fresh water to a cleaning water supply tube 420 and may be selectively opened as needed. The collecting tube 531 may also supply the seawater or the fresh water that has passed through the pretreatment unit 530 to a recirculation tube 510.

FIG. 15 illustrates an open loop mode in which seawater is discharged to the outside after passing through the scrubber, and FIG. 16 illustrates a closed loop mode in which seawater is recirculated through the recirculation tube 510 after passing through the scrubber.

Referring to FIG. 15, some of the seawater introduced through the seawater supply tube 421 is supplied to a scrubber 430 through the cleaning water supply tube 420, and some of the seawater is supplied to a neutralizing agent supply unit 470 through a seawater inlet tube 422. Cleaning water may be sprayed from an upper part of the scrubber 430 and may fill a lower part of the scrubber 430 to a certain level. At this time, exhaust gas supplied through the exhaust gas tube 410 may sequentially pass through the pretreatment unit 530, the oxidation unit 440 and a liquid catalyst injection unit 450 and then be sprayed from the lower part of the scrubber 440. The pretreatment unit 530 may spray the seawater supplied from the seawater supply tube 421 to fine dust, and the seawater that has passed through the pretreatment unit 530 may be supplied to the cleaning water supply tube 420 through the collecting tube 531. The oxidation unit 440 oxidizes nitrogen monoxide contained in the exhaust gas into nitrogen dioxide by discharging electricity, irradiating ultraviolet rays, or spraying an oxidizing agent. The liquid catalyst injection unit 450 maintains the exhaust gas in the oxidized state by injecting a liquid catalyst into the oxidized exhaust gas.

The neutralizing agent supply unit may store or generate a neutralizing agent and spray the neutralizing agent to the seawater supply tube 421, the scrubber 430 or the collecting tube 531.

Since the exhaust gas is sprayed within the cleaning water filling the lower part of the scrubber 430, contaminants such as nitrogen oxides, sulfur oxides and dust can be removed. In addition, the contaminants can be removed again by the cleaning water sprayed from the upper part of the scrubber 430. Through this process, the contaminants contained in the exhaust gas are removed, and the exhaust gas from which the contaminants have been removed is discharged to the outside through a discharge tube 432.

The cleaning water that has passed through the scrubber 430 contains contaminants such as nitrogen oxides, sulfur oxides and dust and is discharged out of the scrubber 430 through a cleaning water discharge tube 431. The liquid catalyst is separated from the cleaning water flowing through the cleaning water discharge tube 431 as the cleaning water passes through a separation unit 460. The separated liquid catalyst may be circulated to the liquid catalyst injection unit 450 through a circulation line 461. The cleaning water from which the liquid catalyst has been separated moves to the filter unit 480. The filter unit 480 separates contaminants such as solid-phase particles from the cleaning water and stores the contaminants in a sludge tank 490. The cleaning water from which the contaminants have been separated is discharged out of a ship through a seawater discharge tube 424.

Referring to FIG. 16, some of the seawater introduced through the seawater supply tube 421 is supplied to the scrubber 430, and some of the seawater is supplied to the neutralizing agent supply unit 470. Cleaning water containing a liquid catalyst and supplied to the cleaning water discharge tube 431 via the scrubber 430 is temporarily stored in a recirculation tank 500 and then supplied back to the cleaning water supply tube 420 through the recirculation tube 510. That is, the remaining process of FIG. 16 is the same as that of FIG. 15 except that the cleaning water containing the liquid catalyst is not discharged out of the ship but is recirculated to the cleaning water supply tube 420 through the recirculation tube 510.

The process of FIG. 16 may be used when the seawater cannot be discharged to the outside, for example, when the ship is passing through an area where the discharge of the seawater is restricted. The process of FIG. 15 and the process of FIG. 16 may be performed selectively or sequentially as needed.

While the inventive concept has been particularly shown and described with reference to exemplary embodiments thereof, it will be understood by those of ordinary skill in the art that various changes in form and detail may be made therein without departing from the spirit and scope of the inventive concept as defined by the following claims. The exemplary embodiments should be considered in a descriptive sense only and not for purposes of limitation.

It is claimed:

1. A contaminant reducing device comprising:
an exhaust gas tube which supplies exhaust gas from a combustion engine;
an oxidation unit which is installed on the exhaust gas tube and oxidizes the exhaust gas by discharging electricity irradiating ultraviolet rays or injecting an oxidizing agent;
a cleaning water supply tube which supplies cleaning water;
a scrubber which sprays the cleaning water supplied through the cleaning water supply tube to the oxidized exhaust gas supplied through the exhaust gas tube;
a cleaning water discharge tube which discharges the cleaning water from the scrubber; and
a recirculation tank which removes solid-phase particles from the discharged cleaning water and stores the solid-phase-free cleaning water,
wherein the solid-phase-free cleaning water stored in the recirculation tank is selectively supplied to the cleaning water supply tube.

2. The device of claim 1, further comprising:
a purification unit which is connected to the exhaust gas tube or the scrubber and electrolyzes seawater to generate hydrogen and an oxidizing agent for oxidizing nitrogen-based oxides or a neutralizing agent for neutralizing acidified cleaning water; and
a fuel cell module which receives the hydrogen from the purification unit and generates electricity.

3. The device of claim 2, wherein the fuel cell module supplies electricity to the purification unit.

4. The device of claim 2, wherein the cleaning water supply tube branches from a seawater supply tube which receives seawater from the outside and further comprising a pump which is installed on the seawater supply tube to pressurize the seawater, wherein the fuel cell module supplies electricity to the pump.

5. The device of claim 2, further comprising an electrolyte tank which is installed on a seawater inlet tube connected to the purification unit and supplies an electrolyte to seawater.

6. The device of claim 1, further comprising a pretreatment unit which is connected to the exhaust gas tube and located in front of the oxidation unit to remove fine dust from the exhaust gas.

7. The device of claim 6, wherein the cleaning water supply tube branches from a seawater supply tube which receives seawater from the outside, the seawater supply tube supplies the seawater to the pretreatment unit, and the supplied seawater is sprayed within the pretreatment unit.

8. The device of claim 6, further comprising a fresh water supply tube which is connected to the cleaning water supply tube to supply fresh water, wherein the fresh water supply tube supplies the fresh water to the pretreatment unit, and the supplied fresh water is sprayed within the pretreatment unit.

9. The device of claim 6, further comprising a collecting tube which supplies the seawater or the fresh water that has passed through the pretreatment unit to the cleaning water supply tube.

10. The device of claim 6, wherein the pretreatment unit comprises a centrifuge which separates the fine dust from the exhaust gas supplied through the exhaust gas tube, wherein the centrifuge is a cyclone solid separator which receives the exhaust gas in a tangential direction.

11. The device of claim 1, further comprising a liquid catalyst injection unit which is connected to the exhaust gas tube behind the oxidation unit or to the cleaning water supply tube and maintains the exhaust gas in an oxidized state by injecting a liquid catalyst.

12. The device of claim 11, wherein the liquid catalyst is organic sulfoxides obtained by oxidizing organic sulfides contained in oil.

13. The device of claim 11, further comprising:
a separation unit which is connected to the cleaning water discharge tube and separates the liquid catalyst from the cleaning water using a difference in specific gravity between the liquid catalyst and the cleaning water; and
a circulation line which connects the separation unit and the liquid catalyst injection unit and circulates the liquid catalyst separated from the cleaning water by the separation unit to the liquid catalyst injection unit.

14. The device of claim 11, further comprising a neutralizing agent supply unit which is connected to the scrubber and supplies a neutralizing agent.

15. The device of claim 11, further comprising a pretreatment unit which is connected to the exhaust gas tube located in front of the oxidation unit and removes the fine dust from the exhaust gas.

* * * * *

UNITED STATES PATENT AND TRADEMARK OFFICE
CERTIFICATE OF CORRECTION

PATENT NO. : 10,786,591 B2  
APPLICATION NO. : 15/758333  
DATED : September 29, 2020  
INVENTOR(S) : Lee et al.

Page 1 of 1

It is certified that error appears in the above-identified patent and that said Letters Patent is hereby corrected as shown below:

In the Specification

Column 2, Line 24: replace "he" with --the--

Column 4, Line 12: add --the-- after "illustrate"

Column 12, Line 54: replace "be" with --exhaust tube--

Column 13, Line 25: replace "ate" with --water--

Column 13, Line 33: replace "gray" with --may--

Column 14, Line 45: replace "he" with --be--

Column 21, Line 47: add --in-- after "generated"

Column 21, Line 6: replace "moray" with --may--

Column 21, Line 13: add --the-- after "to"

Column 25, Line 19: add --can-- after "seawater"

Signed and Sealed this  
Tenth Day of November, 2020

Andrei Iancu  
*Director of the United States Patent and Trademark Office*